United States Patent
Longo et al.

(10) Patent No.: US 9,345,603 B1
(45) Date of Patent: May 24, 2016

(54) DELIVERY DEVICE AND METHOD OF DELIVERY

(71) Applicant: Intact Vascular, Inc., Wayne, PA (US)

(72) Inventors: Michael Longo, Glenmoore, PA (US); Douglas Evans, Downingtown, PA (US); Michael Dotsey, Chester Springs, PA (US)

(73) Assignee: Intact Vascular, Inc., Wayne, PA (US)

( * ) Notice: Subject to any disclaimer, the term of this patent is extended or adjusted under 35 U.S.C. 154(b) by 0 days.

(21) Appl. No.: 14/935,087

(22) Filed: Nov. 6, 2015

Related U.S. Application Data

(63) Continuation of application No. 14/746,636, filed on Jun. 22, 2015, now Pat. No. 9,192,500.

(60) Provisional application No. 62/109,550, filed on Jan. 29, 2015.

(51) Int. Cl.
| | |
|---|---|
| *A61F 2/06* | (2013.01) |
| *A61F 2/966* | (2013.01) |
| *A61F 2/962* | (2013.01) |
| *A61B 19/00* | (2006.01) |

(52) U.S. Cl.
CPC ............... *A61F 2/966* (2013.01); *A61B 19/54* (2013.01); *A61F 2/962* (2013.01); *A61B 2019/5466* (2013.01)

(58) Field of Classification Search
CPC . A61F 2/966; A61F 2/962; A61F 2002/9665; A61F 2002/9517; A61F 2/95; A61F 2002/9505; A61F 2002/9528; A61F 2002/9534; A61F 2/954; A61F 2/2427; A61F 2/2436
See application file for complete search history.

(56) References Cited

U.S. PATENT DOCUMENTS

| | | | |
|---|---|---|---|
| 3,051,172 A | | 8/1962 | Bruchhaus |
| 4,921,484 A | | 5/1990 | Hillstead |
| 4,994,065 A | | 2/1991 | Gibbs et al. |
| 5,160,341 A | | 11/1992 | Brenneman et al. |
| 5,304,121 A | | 4/1994 | Sahatjian |
| 5,397,355 A | | 3/1995 | Marin et al. |
| 5,443,477 A | | 8/1995 | Marin et al. |
| 5,571,135 A | | 11/1996 | Fraser et al. |
| 5,601,568 A | | 2/1997 | Chevillon et al. |
| 5,618,300 A | | 4/1997 | Marin et al. |
| 5,707,376 A | * | 1/1998 | Kavteladze ............... A61F 2/90 623/1.11 |
| 5,725,572 A | | 3/1998 | Lam et al. |
| 5,741,270 A | | 4/1998 | Hansen et al. |
| 5,817,152 A | | 10/1998 | Birdsall et al. |
| 5,833,694 A | | 11/1998 | Poncet |
| 5,944,727 A | | 8/1999 | Ahari et al. |

(Continued)

FOREIGN PATENT DOCUMENTS

| | | |
|---|---|---|
| EP | 0714640 | 6/1996 |
| EP | 1393766 A1 | 3/2004 |

(Continued)

*Primary Examiner* — Jonathan W Miles
*Assistant Examiner* — Chima Igboko
(74) *Attorney, Agent, or Firm* — Knobbe, Martens, Olson & Bear, LLP

(57) ABSTRACT

A delivery device can include a number of different features including, one or more of, but not limited to, the following. Shuttle and trigger retraction of an outer sheath. Arcuate movement of a trigger. An interlock device to prevent actuation of the trigger. An interlock device that can adjust the position of the outer sheath and the inner shaft. A retraction override switch and lock.

15 Claims, 17 Drawing Sheets

(56) References Cited

U.S. PATENT DOCUMENTS

| | | | |
|---|---|---|---|
| 5,968,052 A | 10/1999 | Sullivan, III et al. |
| 5,968,088 A | 10/1999 | Hansen et al. |
| 6,007,543 A | 12/1999 | Ellis et al. |
| 6,036,725 A | 3/2000 | Avellanet |
| 6,110,198 A | 8/2000 | Fogarty et al. |
| 6,123,722 A | 9/2000 | Fogarty et al. |
| 6,126,685 A | 10/2000 | Lenker et al. |
| 6,146,358 A | 11/2000 | Rowe |
| 6,238,402 B1 | 5/2001 | Sullivan et al. |
| 6,338,739 B1 | 1/2002 | Datta et al. |
| 6,391,050 B1 | 5/2002 | Broome |
| 6,402,760 B1 | 6/2002 | Fedida |
| 6,428,566 B1 | 8/2002 | Holt |
| 6,514,261 B1 | 2/2003 | Randall et al. |
| 6,517,573 B1 | 2/2003 | Pollock et al. |
| 6,520,934 B1 | 2/2003 | Lee et al. |
| 6,520,983 B1 | 2/2003 | Colgan et al. |
| 6,599,296 B1 | 7/2003 | Gillick et al. |
| 6,660,031 B2 | 12/2003 | Tran et al. |
| 6,755,854 B2 | 6/2004 | Gillick et al. |
| 7,001,422 B2 | 2/2006 | Escamilla et al. |
| 7,052,511 B2 | 5/2006 | Weldon |
| 7,105,016 B2 | 9/2006 | Shiu et al. |
| 7,166,125 B1 | 1/2007 | Baker et al. |
| 7,172,617 B2 | 2/2007 | Colgan et al. |
| 7,300,456 B2 | 11/2007 | Andreas et al. |
| 7,320,702 B2 | 1/2008 | Hammersmark et al. |
| 7,323,006 B2 | 1/2008 | Andreas et al. |
| 7,326,203 B2 | 2/2008 | Papineau et al. |
| 7,331,992 B2 | 2/2008 | Randall et al. |
| 7,351,255 B2 | 4/2008 | Andreas |
| 7,402,168 B2 | 7/2008 | Sanderson et al. |
| 7,611,497 B2 | 11/2009 | Wollschlager |
| 7,674,282 B2 | 3/2010 | Wu et al. |
| 7,763,063 B2 | 7/2010 | Arbefeuille et al. |
| 7,799,065 B2 | 9/2010 | Pappas |
| 7,896,911 B2 | 3/2011 | Schneider et al. |
| 7,905,913 B2 | 3/2011 | Chew et al. |
| 7,918,880 B2 | 4/2011 | Austin |
| 7,963,987 B2 | 6/2011 | Melsheimer et al. |
| 8,075,607 B2 | 12/2011 | Melsheimer et al. |
| 8,092,468 B2 | 1/2012 | Hansen |
| 8,100,958 B2 | 1/2012 | Fischer et al. |
| 8,128,677 B2 | 3/2012 | Schneider et al. |
| 8,366,766 B2 | 2/2013 | Berreklouw |
| 8,414,636 B2 | 4/2013 | Nabulsi et al. |
| 8,500,789 B2 | 8/2013 | Wuebbeling et al. |
| 8,585,747 B2 | 11/2013 | Andreas et al. |
| 2002/0055772 A1 | 5/2002 | McGuckin, Jr. et al. |
| 2002/0123790 A1 | 9/2002 | White et al. |
| 2002/0143386 A1 | 10/2002 | Davila et al. |
| 2002/0151955 A1 | 10/2002 | Tran et al. |
| 2002/0156496 A1 | 10/2002 | Chermoni |
| 2003/0018377 A1 | 1/2003 | Berg et al. |
| 2003/0225446 A1 | 12/2003 | Hartley |
| 2004/0158308 A1 | 8/2004 | Hogendijk et al. |
| 2004/0186551 A1 | 9/2004 | Kao et al. |
| 2005/0060016 A1 | 3/2005 | Wu et al. |
| 2005/0171592 A1 | 8/2005 | Majercak |
| 2005/0246008 A1 | 11/2005 | Hogendijk et al. |
| 2005/0288764 A1 | 12/2005 | Snow et al. |
| 2005/0288766 A1 | 12/2005 | Plain et al. |
| 2006/0111769 A1 | 5/2006 | Murray |
| 2006/0184225 A1 | 8/2006 | Pryor |
| 2006/0193892 A1 | 8/2006 | Furst et al. |
| 2006/0206190 A1 | 9/2006 | Chermoni |
| 2006/0229700 A1 | 10/2006 | Acosta et al. |
| 2006/0271151 A1 | 11/2006 | McGarry et al. |
| 2006/0276871 A1 | 12/2006 | Lamson et al. |
| 2006/0282149 A1 | 12/2006 | Kao |
| 2007/0088420 A1 | 4/2007 | Andreas et al. |
| 2007/0118201 A1 | 5/2007 | Pappas et al. |
| 2007/0156223 A1 | 7/2007 | Vaughan |
| 2007/0156225 A1 | 7/2007 | George et al. |
| 2007/0179587 A1 | 8/2007 | Acosta et al. |
| 2007/0276461 A1 | 11/2007 | Andreas et al. |
| 2008/0033522 A1 | 2/2008 | Grewe et al. |
| 2008/0051867 A1 | 2/2008 | Davila et al. |
| 2008/0082154 A1 | 4/2008 | Tseng et al. |
| 2008/0091257 A1* | 4/2008 | Andreas ............... A61F 2/95 623/1.11 |
| 2008/0132989 A1 | 6/2008 | Snow et al. |
| 2008/0255653 A1 | 10/2008 | Schkolnik |
| 2008/0264102 A1 | 10/2008 | Berra |
| 2008/0319528 A1 | 12/2008 | Yribarren et al. |
| 2009/0018637 A1 | 1/2009 | Paul, Jr. et al. |
| 2009/0024133 A1 | 1/2009 | Keady et al. |
| 2009/0270967 A1 | 10/2009 | Fleming, III et al. |
| 2009/0276031 A1 | 11/2009 | Kao |
| 2010/0137966 A1 | 6/2010 | Magnuson |
| 2010/0174290 A1* | 7/2010 | Wuebbeling ............ A61F 2/95 606/108 |
| 2010/0318173 A1 | 12/2010 | Kolandaivelu et al. |
| 2011/0004237 A1 | 1/2011 | Schneider et al. |
| 2011/0071621 A1 | 3/2011 | Griego et al. |
| 2011/0077731 A1 | 3/2011 | Lee et al. |
| 2011/0152992 A1 | 6/2011 | Schneider et al. |
| 2011/0301685 A1 | 12/2011 | Kao |
| 2011/0301690 A1 | 12/2011 | Giasolli et al. |
| 2011/0307049 A1 | 12/2011 | Kao |
| 2012/0035705 A1 | 2/2012 | Giasolli et al. |
| 2012/0083872 A1 | 4/2012 | Schneider et al. |
| 2012/0172963 A1 | 7/2012 | Ryan et al. |

FOREIGN PATENT DOCUMENTS

| | | |
|---|---|---|
| WO | WO 96/09013 | 3/1996 |
| WO | WO 01/76509 | 10/2001 |
| WO | WO 03/047651 | 6/2003 |
| WO | WO 2004/032799 | 4/2004 |
| WO | WO 2007/109621 | 9/2007 |

* cited by examiner

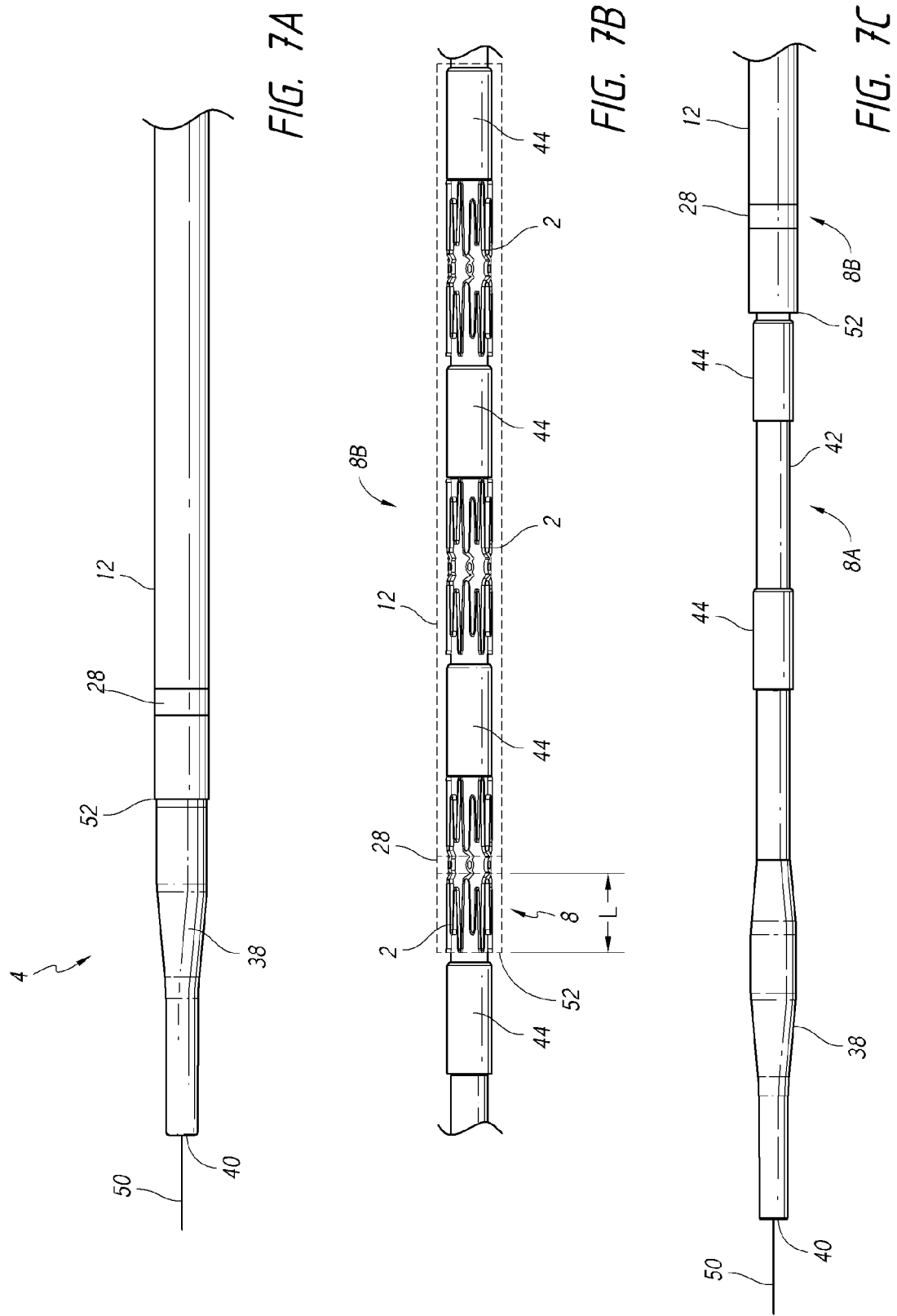

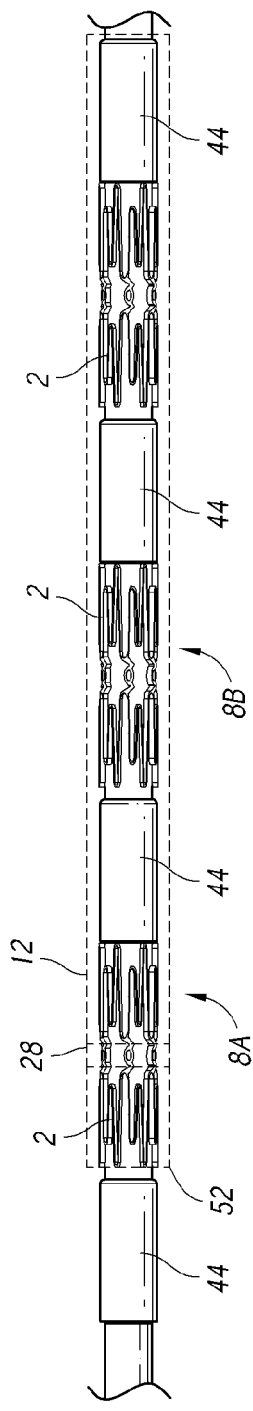
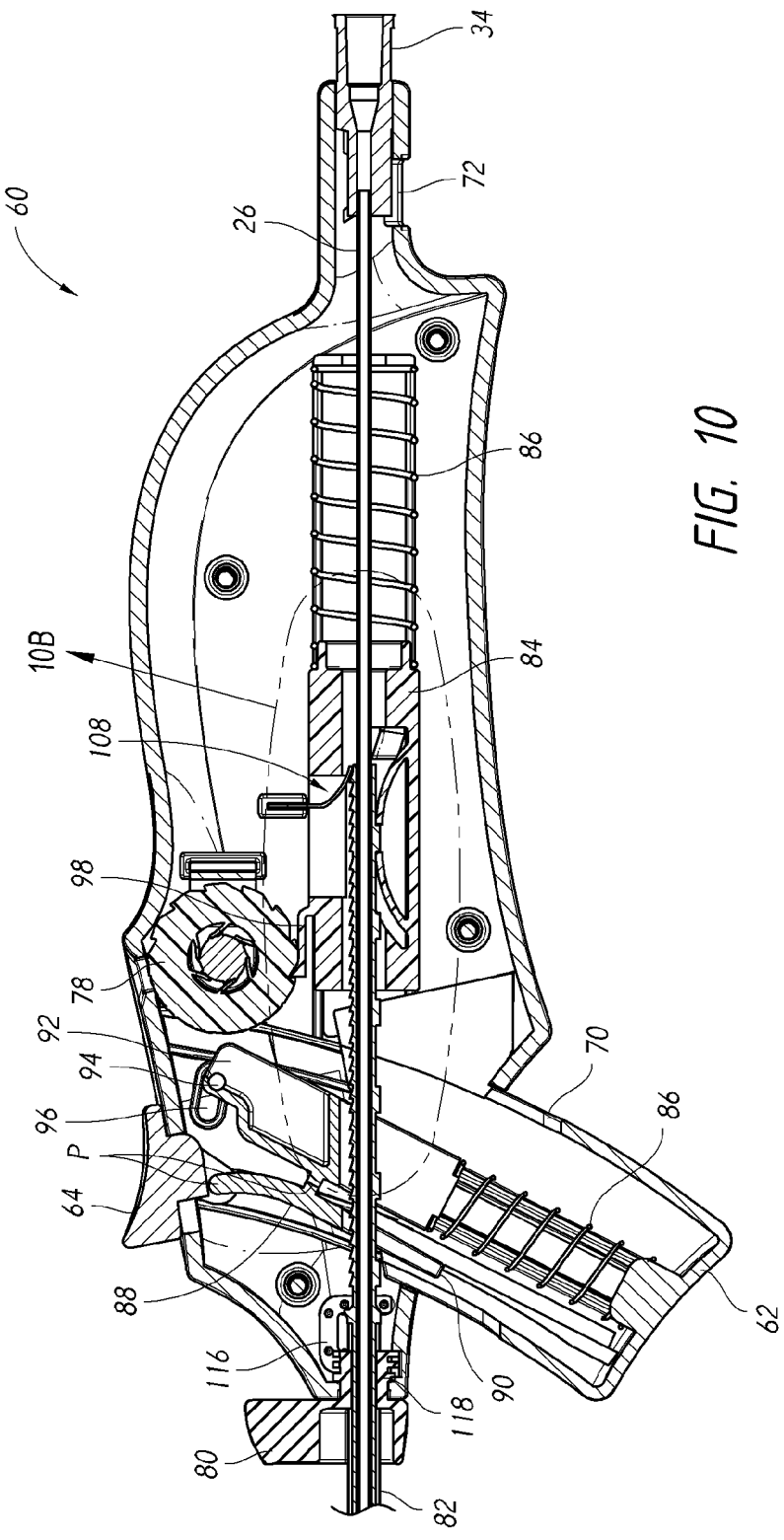
FIG. 10A
FIG. 10

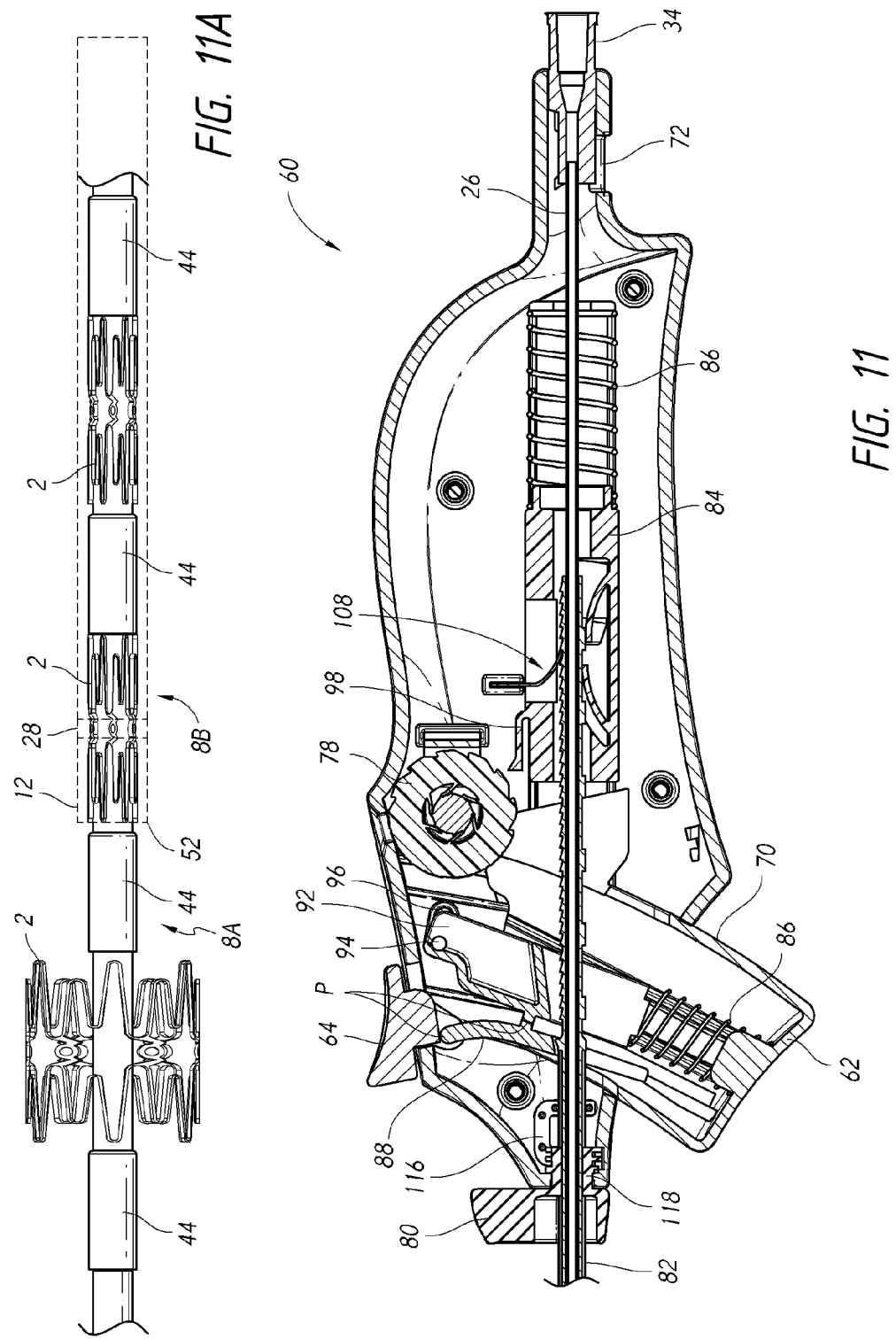

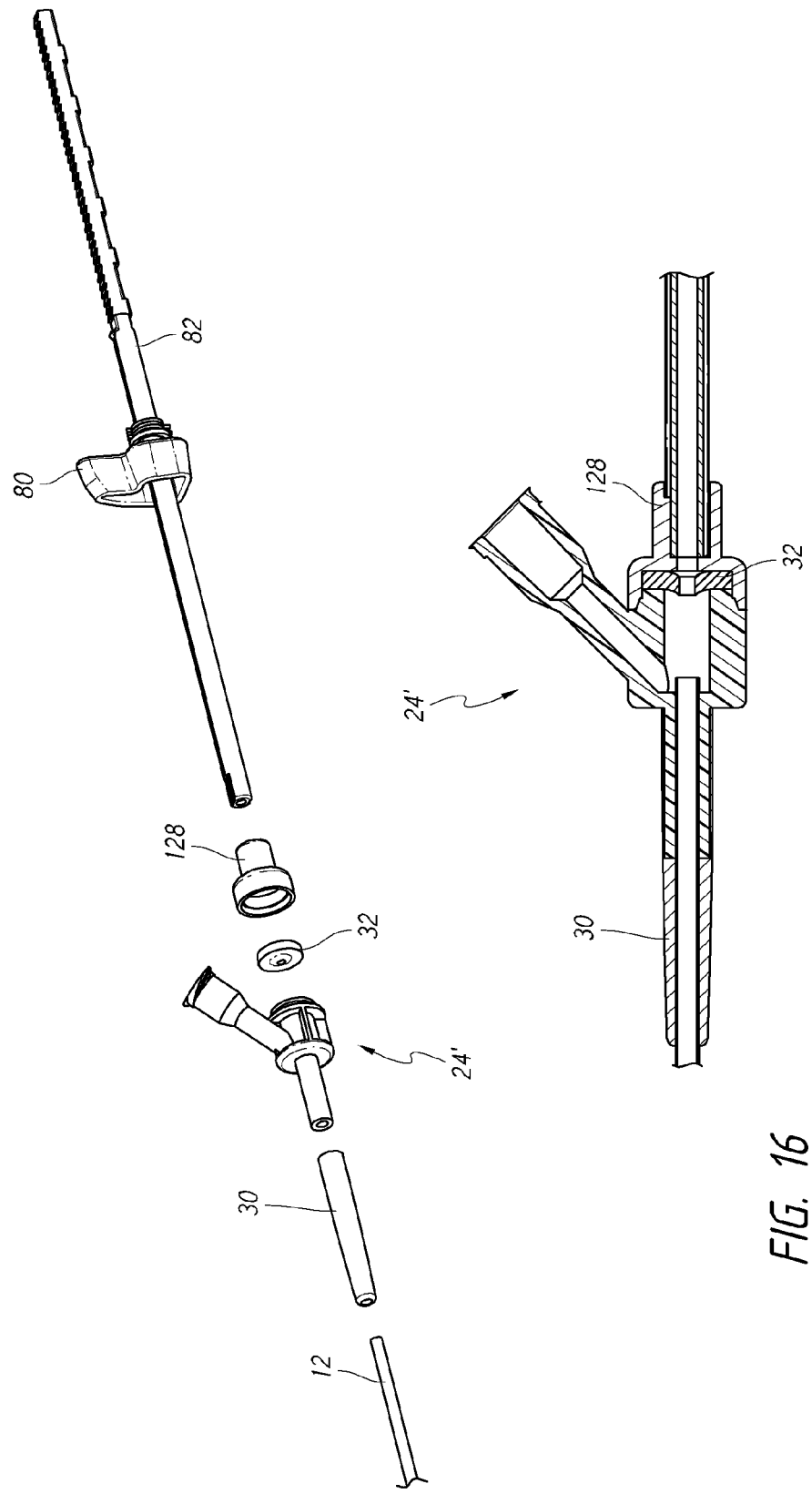

DELIVERY DEVICE AND METHOD OF DELIVERY

INCORPORATION BY REFERENCE TO ANY PRIORITY APPLICATIONS

This application is a continuation of U.S. patent application Ser. No. 14/746,636, filed Jun. 22, 2015, which claims the benefit of priority of U.S. Provisional Appl. No. 62/109,550, filed Jan. 29, 2015. All of the above applications are incorporated by reference herein and are to be considered a part of this specification. Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

Disclosed herein are delivery devices and methods of delivery. Certain embodiments are described with reference to sequential delivery of multiple intraluminal devices from a delivery device. The delivery devices and methods can be used in procedures to treat atherosclerotic occlusive disease, though they are not limited to these procedures.

2. Description of the Related Art

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms a hard layer along the wall of an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY OF THE INVENTION

Currently available stents and stent delivery systems have many limitations and drawbacks. There exists a continuing need for improvement in intraluminal devices and associated delivery devices.

According to certain embodiments, a delivery device can be provided for sequential delivery of a plurality of intraluminal devices (e.g. stents, tacks, staples, etc.) held in a compressed state on the delivery device. For purposes of this disclosure the word tack will be used to describe one of many intraluminal devices which can be deployed from a delivery device. The delivery device can comprise a plurality of delivery platforms, each delivery platform configured for holding a tack in a compressed position on the delivery device and having a unique shape, such as a non-constant outer diameter, an hourglass shape, a tapered proximal half, ridges, dimples, etc. This unique shape can be positioned between annular pusher bands that may also be radiopaque markers.

In some embodiments, the unique shape is provided by a sleeve of flexible material with the unique shape surrounding a harder inner shaft. Further, the annular pusher bands can be made of wire or sections of material to increase flexibility while remaining radiopacity.

A tack deployment method can include alignment of radiopaque markers on the outer sheath and the tack to be deployed prior to deployment.

A method of marker band alignment and intraluminal device or tack delivery can be performed. The method can include: advancing a delivery device with a plurality of tacks in a compressed state to a treatment area; each tack comprising a plurality of struts and a radiopaque marker positioned in a central region of the tack, each tack being a same size with the radiopaque marker positioned in a same location; the delivery device comprising an inner core having a plurality of delivery platforms, each delivery platform having one of the plurality of tacks, and an outer sheath covering the inner core and the delivery platforms, the outer sheath having a radiopaque marker band positioned proximally from a distal end; withdrawing the outer sheath until the radiopaque marker band on the outer sheath and radiopaque marker on a first tack to be delivered are aligned; aligning these two radiopaque markers with a treatment area such as a tissue dissection or lesion to be treated before release of the tack; then withdrawing the outer sheath to release the tack.

In some embodiments, a delivery device can comprise an inner shaft, a delivery platform and an outer sheath. The delivery platform can include a pair of annular bands around the inner shaft, both of the annular bands having a first outer diameter and a sleeve. The sleeve can be secured to the inner shaft and positioned between the annular bands. The sleeve can have a lower durometer than the inner shaft and optimally also lower than the pair of annular bands. The sleeve can further have a non-constant outer diameter being less than the first outer diameter of the annular bands. The delivery platform can be configured to receive an intraluminal device for deployment from the delivery device into a vessel and to receive the intraluminal device between the annular bands and on the sleeve. The outer sheath can be positioned on and slidable over the inner shaft and the delivery platform, the outer sheath having a pre-deployment position covering the delivery platform and at least one delivery position where the outer sheath is withdrawn exposing at least one of the annular bands and the sleeve of the delivery platform.

According to some embodiments, a plurality of additional delivery platforms can be included for sequential delivery of a plurality of intraluminal devices. Each additional delivery platform can comprise an additional sleeve and an additional annular band. Each of the annular bands can have a radius on a proximal end and/or comprise a radiopaque helical coil. The radiopaque helical coil can be encased in a polymer having a higher durometer than a polymer that forms the sleeve.

The sleeve can include any number of different shapes and sizes, and can include ridges, dots, dimples, etc.

In some embodiments, a delivery device can comprise an inner shaft, the inner shaft having a nose cone on the distal tip; a delivery platform; and an outer sheath. The delivery platform can comprise a pair of annular bands secured to the inner shaft, both of the annular bands having a first outer diameter; and a sleeve secured to the inner shaft and positioned between the annular bands. The sleeve can have a lower durometer than the inner shaft and optionally also the pair of annular bands. The sleeve may further have a first constant outer diameter section and a second constant outer diameter section having a larger outer diameter than the first, but less than the first outer diameter of the annular bands, and the second constant outer diameter section having a shorter axial length than the first constant outer diameter section, the sleeve further having a smooth tapered transition between the first and second constant outer diameter sections. The delivery platform can be configured to receive an intraluminal device for deployment from the delivery device into a vessel and configured to receive the intraluminal device between the annular bands and on the sleeve. The outer sheath can be positioned on and slidable over the inner shaft and the delivery platform. The outer sheath can have a pre-deployment position covering the delivery platform and at least one delivery position where the outer sheath is withdrawn exposing at least one of the annular bands and the sleeve of the delivery platform.

An intraluminal device deployment method can include one or more of the following steps. Advancing a delivery device with a plurality of intraluminal devices in a compressed state to a treatment area. Each of the plurality of intraluminal devices can comprise a plurality of struts and a radiopaque marker positioned in a central region of the intraluminal device. Each of the plurality of intraluminal devices can be a same size with the radiopaque marker positioned in a same location. The delivery device can comprise an inner shaft having a plurality of delivery platforms, each intraluminal device of the plurality of intraluminal devices positioned at a respective delivery platform of the plurality of delivery platforms, and an outer sheath covering the inner shaft and the plurality of delivery platforms, the outer sheath having a radiopaque marker band positioned proximally from a distal end of the outer sheath. Withdrawing the outer sheath until the radiopaque marker band on the outer sheath and radiopaque marker on a first intraluminal device to be delivered of the plurality of intraluminal devices are aligned. Aligning the aligned radiopaque marker band and the radiopaque marker with the treatment area before release of the first intraluminal device. Withdrawing the outer sheath to release the first intraluminal device. Withdrawing the outer sheath until the radiopaque marker band on the outer sheath and radiopaque marker on a second intraluminal device to be delivered of the plurality of intraluminal devices are aligned.

In some embodiments of the method, aligning the aligned radiopaque marker band and the radiopaque marker with the treatment area can comprise centering the aligned radiopaque marker band and the radiopaque marker at a tissue dissection before release of the first intraluminal device. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until a distal-most end of the outer sheath and a distal-most end of the first intraluminal device are aligned. In some embodiments of the method, withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band is positioned at a middle of the first intraluminal device. In some embodiments of the method, the first intraluminal device can have a single column of radiopaque markers and withdrawing the outer sheath until the radiopaque marker band on the outer sheath and radiopaque marker on the first intraluminal device to be delivered of the plurality of intraluminal devices are aligned can comprise withdrawing the outer sheath until the radiopaque marker band encircles the single column of radiopaque markers.

In some embodiments, a delivery device can comprise an inner shaft, an outer sheath, an outer sheath rack, a handle housing, a shuttle, and a trigger. The inner shaft can have one or more delivery platforms for deployment of one or more intraluminal devices. The outer sheath can surround the inner shaft and be configured to cover the one or more delivery platforms pre-deployment and to be withdrawn from at least one of the one or more delivery platform as part of a deployment of the one or more intraluminal devices. The outer sheath rack can comprise a plurality of teeth, the outer sheath rack coupled to the outer sheath. The inner shaft and the outer sheath rack are at least partially positioned within the handle housing. The handle housing can include at least one pawl configured to engage with the plurality of teeth on the outer sheath rack to prevent re-sheathing of the outer sheath over the one or more delivery platforms after a deployment. The shuttle can have a pair of deflection arms configured for selective engagement with the plurality of teeth on the outer sheath rack. The trigger can be mechanically linked to the shuttle such that actuation of the trigger causes movement of the shuttle which withdraws the outer sheath from covering the one or more delivery platforms.

According to some embodiments, the plurality of teeth can comprise a first plurality on the top of the rack and a second plurality on the bottom of the rack. The first plurality of teeth can comprise repeating sets of teeth having a first tooth with a greater pitch than the other teeth of the repeating set. The trigger can be configured such that actuation of the trigger from a starting position to an end position withdraws the outer sheath from covering one of the one or more delivery platforms thereby releasing one of the one or more intraluminal devices from the inner shaft. A counter and a shuttle pawl can also be included, wherein the shuttle pawl is configured to engage the counter to change an indication of a number of intraluminal devices available for deployment.

In some embodiments, the handle housing can further comprise an arcuate channel and the trigger is positioned within the arcuate channel to move in an arcuate path. A safety button can be provided to lock the trigger in place such that actuation of the safety button is required to allow actuation of the trigger.

In some embodiments, a control device can be provided for deploying a self-expanding medical device within the vessel of a living being. The control device can comprise a restraining sheath and a control mechanism. The restraining sheath can have a proximal end and a distal end, the restraining sheath being adapted to extend over one or more self-expanding medical devices to maintain the medical devices in a collapsed position and to be retractable to expose the one or more collapsed medical devices for deployment. The control mechanism can include an actuation assembly coupled to the proximal end of the restraining sheath for retracting the restraining sheath, a slider assembly being movable in an arcuate path of motion, the retraction of the restraining sheath being actuated by an actuating force applied by a user to a movable component of the control mechanism which moves in an arcuate path thereby changing the angle of force application and the mechanical advantage of the force applied by a user depending on the location of the movable component along the arcuate path.

A delivery device according to some embodiments can include an inner shaft, an outer sheath, a handle housing, an interlock and a ramp interface. The inner shaft can have one or more delivery platforms for deployment of one or more intraluminal devices. The outer sheath can surround the inner shaft and be configured to cover the one or more delivery platforms pre-deployment and to be withdrawn from one of the one or more delivery platforms as part of a deployment of one of the one or more intraluminal devices. The handle housing can have a trigger mechanically linked to the outer sheath such that actuation of the trigger withdraws the outer sheath from covering one of the one or more delivery platforms. The interlock when in a locked position is engaged with the trigger and the inner shaft to thereby prevent movement of the outer sheath. The ramp interface can be between the interlock and the inner shaft, wherein the ramp interface is configured to adjust the position of the inner shaft relative to the outer sheath when the interlock is removed from engagement with the inner shaft.

In some embodiments, the interlock can engage the trigger with a distal end of the interlock and engage the inner shaft with a proximal end. The proximal end can engage the inner shaft and the handle housing. The distal end of the interlock can be hook shaped. The ramp interface can comprise a first ramp on a protrusion of the interlock and a second ramp on the inner shaft, wherein sliding disengagement of the first and second ramps forces the inner shaft to move.

According to some embodiments, a delivery device can include an inner shaft, an outer sheath, an outer sheath rack, a handle housing, and a retraction override switch. The inner shaft can have one or more delivery platforms for deployment of one or more intraluminal devices. The outer sheath can surround the inner shaft and be configured to cover the one or more delivery platforms pre-deployment and to be withdrawn from one of the one or more delivery platform as part of a deployment of one of the one or more intraluminal devices. The outer sheath rack can comprise a plurality of teeth, the outer sheath rack coupled to the outer sheath, such as at the proximal end. The inner shaft and the outer sheath rack are at least partially positioned within the handle housing. The handle housing can comprise at least one pawl configured to engage with the plurality of teeth on the outer sheath rack to prevent re-sheathing of the outer sheath over the one or more delivery platforms after a deployment. The retraction override switch can be coupled to the outer sheath rack and the inner shaft, wherein actuation of the retraction override switch is configured to disengage the at least one pawl from the plurality of teeth on the outer sheath rack to allow re-sheathing of the outer sheath over the one or more delivery platforms after a deployment.

In some embodiments, the delivery device can further comprise a retraction override lock feature, wherein the retraction override lock is configured to lock the retraction override switch in the actuated position with the at least one disengaged from the outer sheath rack. The retraction override lock can comprise a spring metal plate and the retraction override switch further comprises a cam engaged with the spring metal plate, actuation of the cam can move the cam to a locked position that prevents further movement. The outer sheath rack and outer sheath can be coupled to the retraction override switch such that actuation of the retraction override switch causes the outer sheath rack to move out of engagement with the at least one pawl. The retraction override switch can be configured such that actuation of the retraction override switch causes the retraction override switch to rotate with respect to the handle housing. The outer sheath rack can be configured such that actuation of the retraction override switch causes the outer sheath rack and the outer sheath to rotate with respect to the handle housing.

In some embodiments, a system is provided for deploying two or more intraluminal devices within the vessel of a living being. The system can comprise two or more intraluminal devices. Each intraluminal device may comprise at least one radiopaque marker. An inner shaft of the system can have a proximal end and a distal end, the distal end having two or more delivery platforms for deployment of the two or more intraluminal devices, each intraluminal device in a collapsed state and located in a separate delivery platform. A restraining sheath can be provided having a proximal end and a distal end, the restraining sheath being adapted to extend over the one or more intraluminal devices to maintain the intraluminal devices in a collapsed position and to be retractable to expose the one or more collapsed intraluminal devices for deployment. The restraining sheath may further comprise a sheath radiopaque marker in a distal portion of the sheath located at a set distance with respect to the most distal intraluminal device. A control mechanism can include an actuation assembly coupled to the proximal end of the restraining sheath for retracting the restraining sheath with respect to the inner shaft. The retraction of the restraining sheath can be actuated by an actuating force applied by a user to a movable trigger component of the control mechanism. Actuation of the trigger from a starting position to an end position can completely withdraw the outer sheath from covering one of the one or more delivery platforms thereby releasing one of the one or more intraluminal devices from the inner shaft into a location within living being. This can also locate the sheath radiopaque marker at the distal end of the restraining sheath the set distance with respect to the remaining most distal intraluminal device.

BRIEF DESCRIPTION OF THE DRAWINGS

Various embodiments are depicted in the accompanying drawings for illustrative purposes, and should in no way be interpreted as limiting the scope of the inventions, in which like reference characters denote corresponding features consistently throughout similar embodiments.

FIG. 3A shows a flattened section of the tack of FIG. 3.

FIGS. 7A-C illustrate certain steps of a deployment method.

FIG. 10 is a side view of the handle of FIG. 9 in a first position.

FIG. 10A is a representation of a portion of the distal end of the delivery device when the handle is in the first position of FIG. 10.

FIG. 11 is a side view of the handle of FIG. 9 in a second position.

FIG. 11A is a representation of a portion of the distal end of the delivery device when the handle is in the second position of FIG. 11.

FIG. 16 shows a cross-section of another embodiment of proximal luer hub.

FIG. 16A is an exploded view of the proximal luer hub and other parts of a delivery device.

DETAILED DESCRIPTION OF THE PREFERRED EMBODIMENT

A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow. It will be understood that though the delivery devices and methods described herein are described primarily with reference to vascular procedures, they can also be used in treatments for other parts of the body.

Figure 1:
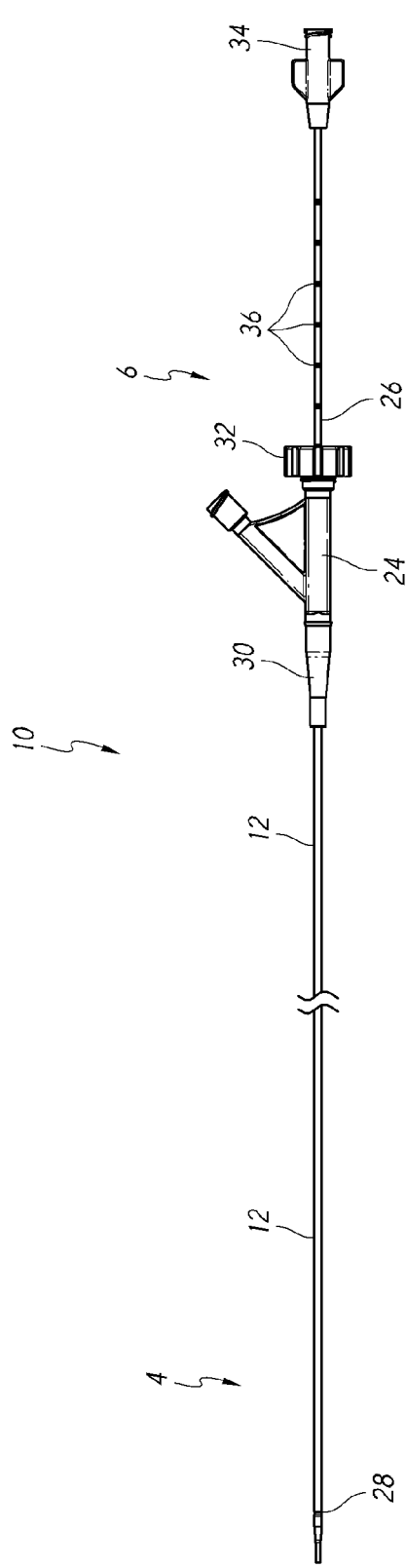
FIG. 1 is a side view of a delivery device that has been shortened to facilitate illustration.
Figure 2:
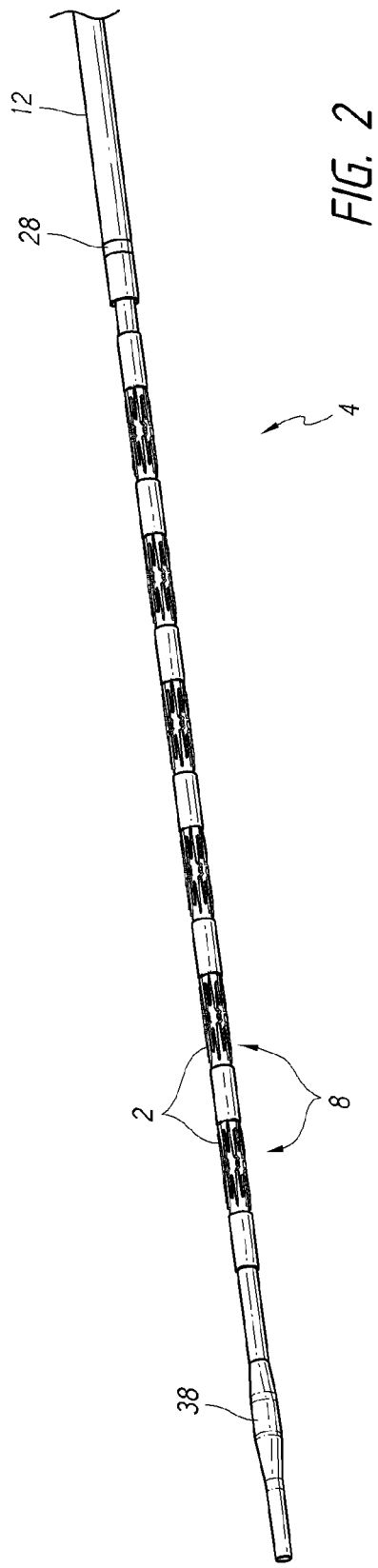
FIG. 2 shows a view of the distal end of the delivery device with an outer sheath withdrawn.

FIGS. 1 and 2 illustrate an embodiment of delivery device 10 that can be used for sequential delivery of multiple intraluminal devices 2. The delivery device 10 can be used in procedures to treat atherosclerotic occlusive disease, though it is not limited to these procedures.

The delivery device 10 of FIG. 1, which has been shortened to facilitate illustration, highlights the distal 4 and proximal ends 6. The proximal end 6 can be held by a physician or other medical professional during a medical procedure. It is used to control delivery of one or more intraluminal devices or tacks 2. FIG. 2 shows the distal end 4 with six (6) intraluminal devices 2, each positioned at a dedicated delivery platform 8. Comparing FIGS. 1 and 2, it can be seen that an outer sheath 12 has been withdrawn from the distal end in FIG. 2. This reveals the delivery platforms 8 and the respective intraluminal devices 2. The intraluminal devices 2 are preferably self-expandable and are shown in their compressed position to represent how they would fit in the delivery platforms. In typical use, the outer sheath 12 would be covering the intraluminal devices 2 when in this position. As will be discussed in more detail below, the outer sheath 12 can be withdrawn in a systematic manner to deploy one intraluminal device 2 at a time at a desired treatment location.

Figure 3:
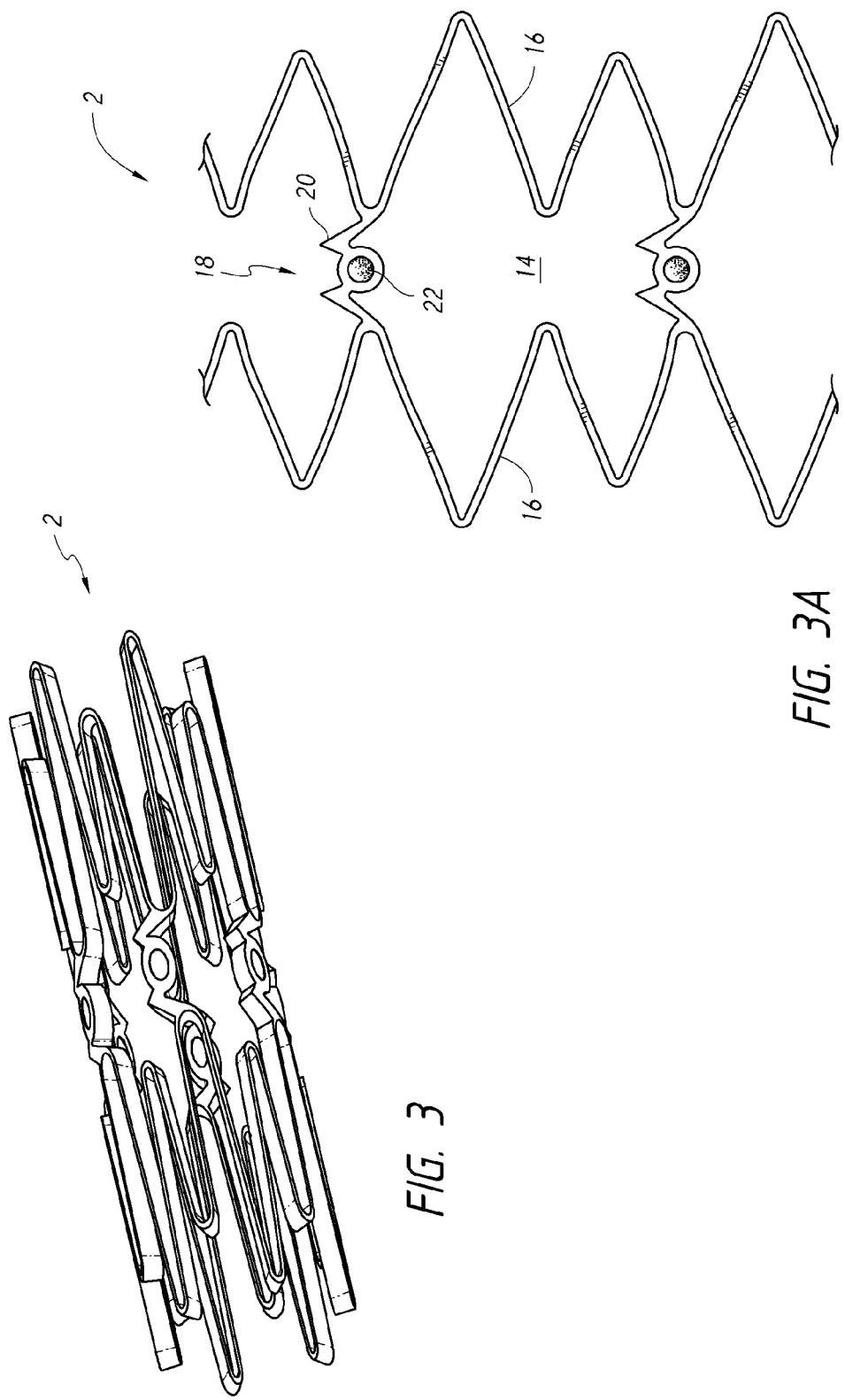
FIG. 3 shows an embodiment of intraluminal device or tack.

Relatively small intraluminal devices 2, for example with only one (FIGS. 3 & 3A) or two columns of cells, can be delivered at precise treatment locations and space appropriately to not overlap. FIG. 3A shows a flattened section of the tack of FIG. 3. It can be seen that a single column of cells 14 are formed by two concentric rings of undulating struts 16 connected by bridge members 18. The bridge members 18 have a pair of anchors 20 and a radiopaque marker 22. Multiple small intraluminal devices 2 can be used to treat a single or multiple lesions. This can minimize the amount of foreign material in the body, while providing needed holding forces. Various embodiments of intraluminal devices and delivery devices are described in more detail in Applicants' related patent application Ser. No. 13/179,458 filed Jul. 8, 2011, published as US 2012/0035705 (IVAS.002P4) and patent application Ser. No. 13/749,643 filed Jan. 24, 2013, published as US 2013/0144375 (IVAS.002P6), both of which are incorporated by reference herein and made a part of this specification.

Each radiopaque marker can be press-fit or swaged into a circular eyelet on the respective bridge member of the intraluminal device. Swaging is a forging process in which the dimensions of an item are altered using dies into which the item is forced. Swaging is usually a cold working process; however, it is sometimes done as a hot working process. Swaging is normally the method of choice for precious metals since there is no loss of material in the process. The radiopaque markers discussed herein with respect to the intraluminal devices and delivery devices can be any number of different materials, including gold, platinum and tantalum.

It will be understood, that the delivery devices and methods can also be used for other intraluminal devices 2, including larger devices, and are not limited to use with intraluminal devices 2 having only one or two columns of cells.

Returning now to FIG. 1, the proximal end 6 of the illustrated embodiment will now be described. The delivery device 10 can include an outer sheath 12, a proximal housing 24, and an inner shaft 26. The outer sheath 12 can be constructed as a laminate of polymer extrusions and braided wires embedded in the polymer extrusions. Flexibility and stiffness can be controlled through the number of braid wires, the braid pattern and pitch of the braid. In other embodiments, the outer sheath can be formed of a hypotube, such as a metal or plastic hypotube. Flexibility and stiffness of the sheath can be controlled by many features such as the slope and frequency of a spiral cut along the length of the hypotube. The outer sheath may also include a radiopaque (RO) marker 28 at or near the distal end. In some embodiments, the radiopaque marker 28 can be an annular band spaced from the distal-most end.

As shown, the outer sheath 12 is a braided shaft and the proximal housing 24 is a bifurcation luer that connects to the outer sheath through a strain relief 30. The strain relief 30 can take any form, such as being made of polyolefin or other similar material.

The bifurcation luer 24 has a main arm to receive the inner shaft 26 and a side arm. The bifurcation luer can be disposed at the proximal end of the outer sheath. The side arm includes a flushing port that is used to flush out air and increase lubricity in the space between the sheath and the inner shaft.

A tuohy borst adapter, hemostatic valve, or other sealing arrangement 32 can be provided proximal of or integrated into the bifurcation luer 24 to receive and seal the proximal end of the space between the inner shaft 26 and the outer sheath 12. The tuohy borst adapter can also provide a locking interface, such as a screw lock, to secure the relationship between the outer sheath and the inner shaft. This can allow the physician to properly place the distal end without prematurely deploying a tack.

The inner shaft is shown with a proximal luer hub 34 and deployment reference marks 36. The deployment reference marks 36 can correspond with the delivery platforms 8, such that the spacing between each deployment reference mark can be the same as the spacing between features of the delivery platforms. For example, the space between deployment reference marks can be the same as the distance between the centers of the delivery platforms.

In some embodiments, a distal most deployment reference mark, or a mark that is different from the others, such as having a wider band or different color, can indicate a primary or home position. For example a deployment reference mark with a wider band than the others can be aligned with the proximal end of the bifurcation luer 24 or hemostatic valve 32. This can indicate to a physician that the outer sheath is in a position completely covering the inner shaft 26 proximal of the nose cone 38. In some embodiments, this alignment can also translate to alignment of the RO marker 28 on the outer sheath to a RO marker on the distal end of the inner shaft 26.

In some embodiments, one or more of the deployment reference marks 36 can represent the number of tacks that are within the system. Thus, once a tack is released, the deployment reference mark 36 will be covered up and the physician can know that the remaining deployment reference marks correspond with the remaining number of tacks available for use. In such an embodiment, the proximal end of the bifurcation luer 24 or hemostatic valve 32 can be advanced to be centered approximately between two reference marks to indicate deployment.

Figure 4:
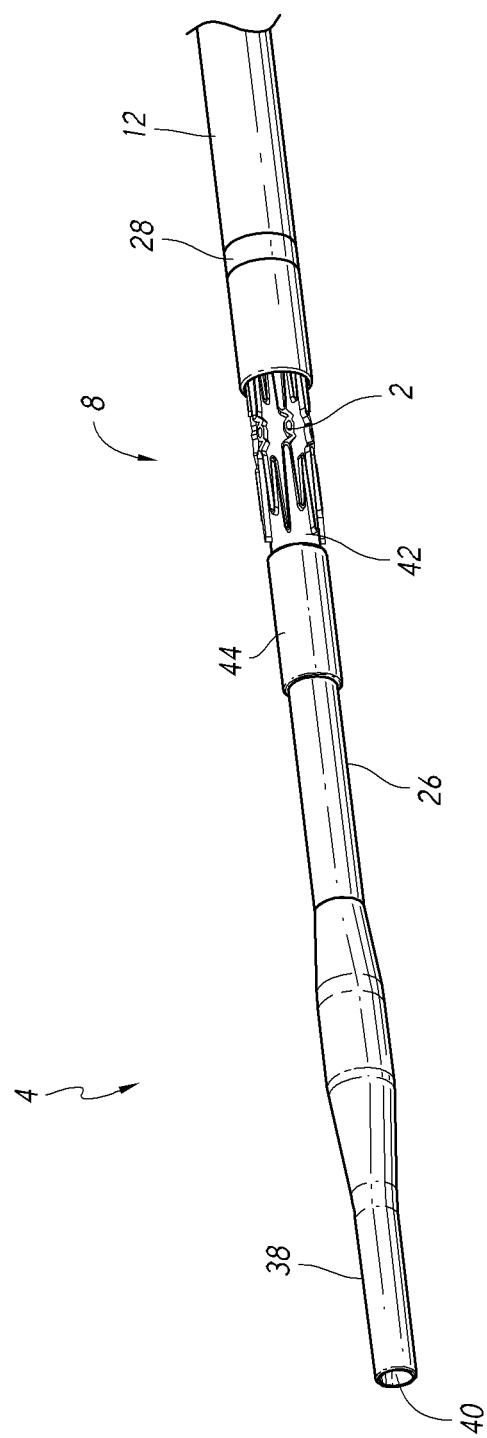
FIG. 4 illustrates a detail view of the distal end of the delivery device with the outer sheath partially withdrawn.

Looking now to FIG. 4, a detail view of the distal end 4 of the delivery device 10 is shown. Features of the illustrated embodiment include the inner shaft 26 with a distal soft tip 38. The tip 38 can be a tapered nose cone. The nose cone 38 serve as a dilating structure to atraumatically displace tissue and help to guide the delivery device through the vasculature. The tip itself 38 may be radiopaque, or a radiopaque element 27 can be incorporated into or near the tip. A guidewire lumen 40 can be seen that extends through the inner shaft 26 to the proximal luer hub 34 (FIG. 1). The guidewire lumen 40 is configured for receipt and advancement of a guidewire therein.

Parts of a delivery platform 8 are also shown. The delivery platforms 8 are identical in the illustrated embodiment, though other embodiments can have different sizes and constructions between different delivery platforms. A crimped or compressed tack 2 is shown in the delivery platform 8.

Figure 5:
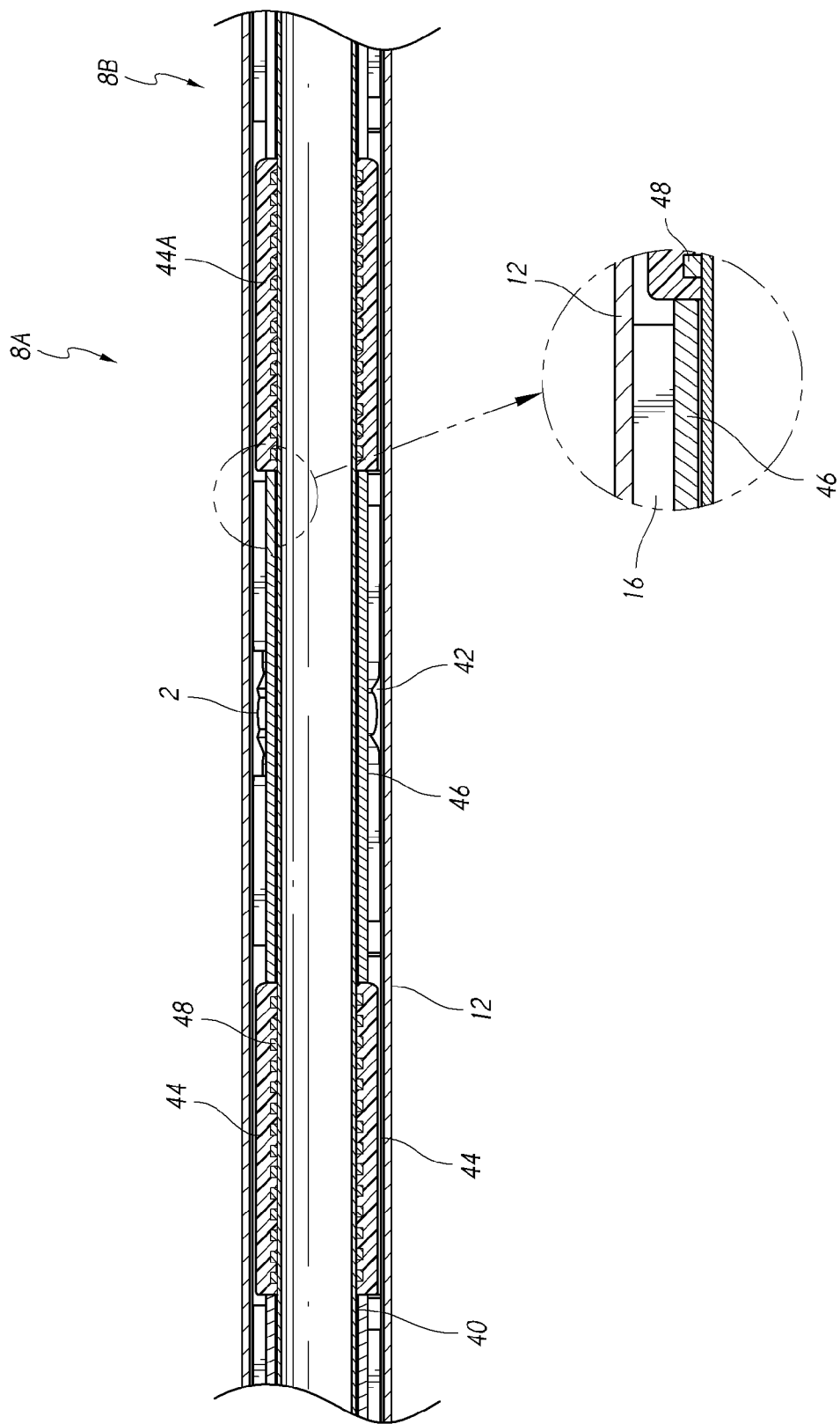
FIG. 5 is a cross section of a delivery device showing an embodiment of delivery platform.

As can be seen in FIGS. 2 and 4, one or more delivery platforms 8 can be disposed on the inner shaft 26 adjacent the distal end 4 of the delivery device 10. Each of the delivery platforms 8 can comprise a recess 42 extending positioned between a pair of annular pusher bands 44. FIG. 5 shows a cross section of a delivery device at one embodiment of delivery platform 8A. In the illustrated embodiment, the proximal annular pusher band 44A of a first platform 8A is also the distal annular pusher band 44A of the platform 8B located immediately proximal (only partially shown). The annular pusher band 44 has a larger outer diameter as compared to the delivery platform at the recess 42. In some embodiments, the recess can be defined as the smaller diameter region next to, or between, one or two annular pusher bands and/or an additional feature on the inner shaft 26.

One or more of the annular pusher bands 44 can be radiopaque marker bands. For example, proximal and distal radiopaque marker bands 44 can be provided to make the ends of the platform 8 visible using standard visualization techniques. The annular marker bands 44 can take any suitable form, for example including one more of tantalum, iridium, and platinum materials. In some embodiments, the pusher bands 44 can be 4 mm long with 6.75 mm recesses between them. A tack of 6.5 mm can be positioned between the pusher bands 44. In some embodiments, the pusher bands can be between 50-70% of the size of the recess and/or the tack. In some embodiments, the pusher bands are about 60%. In other embodiments, the pusher bands can be much smaller, at between 10-20% of the size of the recess and/or the tack. This may be the case especially with longer tacks. In some embodiments, at least the proximal ends of the pusher bands 44 can have a radius to help reduce potential for catching on deployed tacks during retraction of the delivery device.

Reducing the difference in length between the recess and the tack can increase the precision of placement of the tack, especially with tacks having only one or two columns of cells. In some embodiments, the recess can be less than 1, 0.5, 0.4, 0.3, 0.25, or 0.2 mm longer than the tack. The tack can be any number of different sizes, such as 4, 5, 6, 6.5, 8, 10, or 12 mm in length.

The outer sheath 12 can be made of polyether block amide (PEBA), a thermoplastic elastomer (TPE) available under the trade name PEBAX. In some embodiments, the outer sheath 12 can have a thinner inner liner made of a polytetrafluoroethylene (PTFE) such as TEFLON. Any radiopaque marker band(s) 28, or other radiopaque material may be positioned between these two layers. In other embodiments, the radiopaque marker band(s) 28, or other radiopaque material can be embedded within one or more layers of the outer sheath 12. The radiopaque marker band(s) 28 can range from 0.5 mm to 5 mm wide and be located from 0.5 mm to 10 mm proximal from the distal-most tip 52. In some embodiments, the radiopaque marker band(s) 28 can be 1 mm wide and 3 mm proximal from the distal-most tip 52.

In the cross section of FIG. 5 it can be seen that a sleeve 46 is positioned around the inner shaft 26 between the two annular bands 44. In some embodiments, a delivery platform 8 can comprise a sleeve 46 surrounding a shaft 26, where the sleeve 46 is made of a different material, or has different material properties, than the shaft 26. In some embodiments, the sleeve provides a material having a tackiness, a grip, a tread pattern, and/or other features to help the tack stay in place in the delivery platform. In some embodiments, the sleeve can be made of PEBA. The inner shaft according to some embodiments is a composite extrusion made of a PTFE/polyimide composite. The sleeve can be softer than (a lower durometer than) the inner shaft and/or the pusher bands 44. This may be the case even if made of similar types of materials. In some embodiments, the sleeve can be a material having a tackiness, a grip, a tread pattern, and/or other features to help the tack stay in place (e.g. longitudinal position with respect to the inner shaft) while the outer sleeve 12 is withdrawn. This can increase the amount of control during deployment and reduce the likelihood that the tack will shoot out distally from the delivery platform (known in the industry as watermelon seeding). In some cases the outer sheath can be partially removed thereby partially exposing an intraluminal device whereby the intraluminal device can partially expand while being securely retained by the delivery prior to full release.

The sleeve 46 can be sized so that with the tack 2 in the delivery platform 8 there is minimal to no space between the tack and the outer sheath. In some embodiments, the sleeve 46 can be co-molded with or extruded onto the inner shaft 26. In some embodiments, the delivery device 10 can be formed with a single sleeve 46 extending over a length of the inner shaft 26. For example, the sleeve can extend from the first delivery platform to the last delivery platform. The annular bands 44 may surround distinct sections of sleeve 46, or they may be encased by the sleeve 46. In some embodiments, each delivery platform 8 has a separate sleeve 46 positioned in the recess 42. The annular bands 44 may be encased by a different material, or may not be encased at all.

Figure 6A:
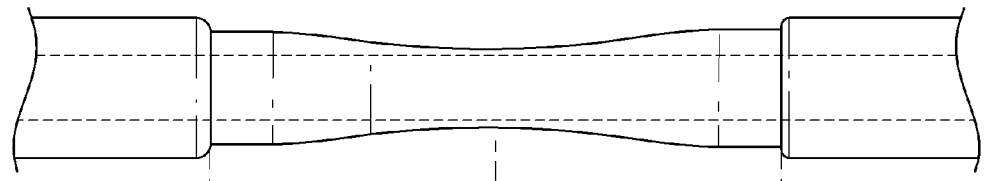
FIGS. 6A-E illustrate various embodiments of delivery platforms having different shapes.
Figure 6B:
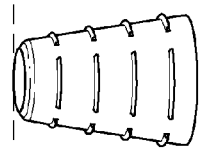
Figure 6C:
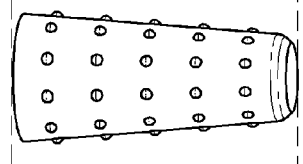
Figure 6D:
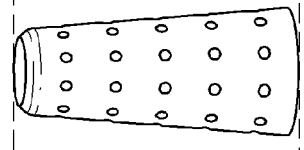

As will be understood from FIG. 5, the sleeve 46 can be cylindrical with a circular cross-section that is maintained across a portion of or the entire length of sleeve. In other embodiments, the sleeve has a unique shape and may include one or more of the following: tapering (FIGS. 6A-E), an hourglass shape (FIG. 6A), ridges (FIG. 6B), dimples (FIG.

6C), dots (FIG. 6D), two or more different diameters (FIG. 6E), etc. Features such as ridges, dots, and dimples can be positioned in number of different patterns or groupings. In addition, the sleeve (FIGS. 6B-D), or a section of the sleeve (FIG. 6E) can extend along less than the entire recess. In some embodiments, the length of the sleeve or larger outer diameter section can correspond to the length of the tack. For example, the sleeve or larger diameter section can extend ¾, ⅔, ½, ⅖, ⅓, ¼ of the recess and/or tack. Further, the length of the sleeve or larger outer diameter section can be related to the size of struts in the undulating ring 16, such as a proximal most undulating ring. For example, it can extend along the entire, ⅘, ¾, ⅔, or ½ of the length of a strut or the length of the proximal most undulating ring. A short sleeve, or a larger outer diameter section of a sleeve, preferably extends from the proximal end of the recess distally (FIGS. 6D-E), but can also be centered in the recess, positioned on at the distal end (FIG. 6C), or at other positions within the recess.

Figure 6E:
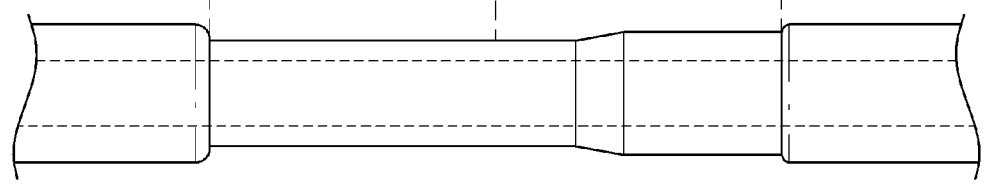

The sleeve of FIG. 6E is shown having two different constant outer diameter sections with a short taper between them. The sleeve can be formed from two separate sections that are thermally bonded together. The tapered portion can also be created by thermal bonding so that there is a smooth transition between the two constant outer diameter sections. As has been mentioned, the larger constant outer diameter section preferably extends from the proximal end of the recess distally. This larger outer diameter section that may or may not have a constant outer diameter can extend along less than the entire recess as has been discussed above.

In some embodiments, an inner shaft 26 can have a lower durometer sleeve 46 between pushers 44. A tack 2 can be crimped onto the sleeve 46 and an outer sheath 12 can constrain the crimped tack in place. The clearance between the sleeve 46 and the outer sheath 12 can result in a slight interference fit between the crimped tack 2 and the inner and outer elements. This slight interference allows the delivery system to constrain the crimped tack during deployment until it is almost completely unsheathed allowing the distal portion of the tack to "flower petal" open and engage the vessel wall, reducing the potential for jumping.

According to some embodiments, the inner shaft 26 can be made of a polyimide-PEBA combination and the lower durometer PEBA sleeve 46 can be thermally bonded in between pushers 44. A tack 2 can be crimped onto the sleeve 46 and a PTFE lined outer sheath 12 can constrain the crimped tack in place.

Returning to FIG. 5, a feature of certain embodiments of radiopaque marker band 44 is shown. As has been mentioned, the sleeve 46 may encase the annular bands 44. Alternatively, another material can encase the metallic bands to form the annular marker bands 44. The annular marker bands 44 can be made of wire 48 or multiple pieces of material or having slits to increase flexibility while remaining radiopacity. In some embodiments the wire can form a helical coil that is wrapped around the inner shaft 26.

Moving now to FIGS. 7A-C, certain methods of deployment will now be described. A delivery device 10 can be used as part of a procedure to treat atherosclerotic occlusive disease. The delivery device can be used to deliver one or more intraluminal devices 2, such as tacks, to a site of plaque accumulation. The tacks can stabilize the site and/or hold pieces of plaque out of the way of blood flow.

The tacks are preferably self-expandable. Thus, withdrawing the sheath 12 to reveal a tack 2 allows the tack to deploy from the delivery device 10 by self-expansion. The sheath can be withdrawn in small increments to sequentially deliver tacks at desired locations in a blood vessel. In some embodiments, the small increments can correspond with the deployment reference marks 36. The deployment reference marks 36 can be spaced apart at least the length of the tack, so that each tack can be deployed at once, rather than the gradual release typical of a longer stent. This can allow for more precise placement of the tack.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. In some instances the balloon is coated with, or otherwise configured to deliver, a drug or biologic to the tissue. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty can form a dissection. More generally, a dissection occurs when a portion of the plaque or tissue is lifted away from the artery, is not fully adherent to the artery and may be mobile or loose. The plaque or tissue that has been disrupted by dissection protrudes into the flow stream. If the plaque or tissue lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is beneficial to place a metal retaining structure, such as a stent or other intraluminal device to hold open the artery after angioplasty and/or force the dissected material back against the wall of the blood vessel to create an adequate lumen for blood flow.

A variety of delivery methodologies and devices can be used to deploy an intraluminal device, such as a tack 2, some of which are described below. For example, a tack can be delivered into the blood vessel with an endovascular insertion. The delivery devices for the different embodiments of plaque tacks can be different or the same and can have features specifically designed to deliver the specific tack. The tack and installation procedure may be designed in a number of ways that share a common methodology of utilizing an expansion force of the delivery mechanism (such as balloon expansion) and/or the expansion force of an undulating ring to enable the tack to be moved into position in the blood vessel, then released to an expanded state within the blood vessel. A tack deployment method can include alignment of radiopaque markers on the outer sheath and the tack to be deployed prior to deployment.

Referring now FIG. 7A, a delivery device 10 with an outer sheath 12 is shown in a first pre-deployment position. Multiple tacks 2 can be held by the outer sheath 12 in a compressed state within the delivery device 10. In some embodiments, the tacks 2 are flash frozen in their compressed state to facilitate loading onto the delivery device. The tacks can extend over a given length of the delivery device as has been described.

The delivery device can be advanced over a guidewire 50 in a patient's vasculature to a treatment site. The guidewire 50 can be the same guidewire used in a prior step of a procedure, such as the guidewire used to position an angioplasty balloon. Once positioned at the treatment location, the outer sheath 12 can be withdrawn or retracted to second pre-deployment position (FIG. 7B). The second pre-deployment position can be used to adjust the position of the outer sheath to account for any stretching, tortuosity, etc. that may require some adjustment before releasing a tack. In the second pre-deployment position, the distal end 52 of the outer sheath can be positioned at, or slightly distal of the distal end of a tack to be deployed.

According to some embodiments, the outer sheath 12 can have a radiopaque annular marker band 28 and the tack can also have one or more radiopaque markers 22. The radiopaque markers 22 can be positioned in a column around the tack. The distance "L" from the distal end of the tack to the radiopaque marker 22 can be the same as the distance from the distal end 52 of the outer sheath 12 to the radiopaque annular marker band 28. In some embodiments, this distance is to the center of the markers 22 and marker band 28. In some embodiments, the length "L" on the outer sheath is at least as long as the length "L" on the tack, if not slightly longer. The outer sheath can be free from other radiopaque markers. In addition, the tack can also be free from other radiopaque markers or columns of radiopaque markers. Thus, the outer sheath can have only a single marker band 28 at the distal end that is spaced from the distal-most end 52 of the outer sheath 12 by at least a distance from the distal-most end of the tack 2 to a radiopaque marker 22 or column of radiopaque markers. In the illustrated embodiment, the radiopaque marker 22 or column of radiopaque markers are positioned in the middle of the device. The radiopaque markers are also positioned on bridge members 18 that connect adjacent rings of undulating struts 16. In some embodiments, the radiopaque marker 22 or column of radiopaque markers can be spaced from the distal-most end of the tack by at least one ring of undulating struts 16. In the illustrated embodiment, the radiopaque marker 22 or column of radiopaque markers is not at the distal-most end of the tack 2, but is spaced therefrom.

Having corresponding radiopaque markers 22, 28 on the tack and the outer sheath can allow the physician to align the markers 22, 28 prior to deployment of the tack. Further, the physician can align the aligned markers with the desired area to be treated. As will be understood, all of this alignment can be done using standard visualization techniques. As has been mentioned, the annular pusher bands 44 on the inner shaft can also be radiopaque. In some embodiments, the pusher bands 44 can be identical and can appear different under visualization than both the marker on the outer sheath and the marker on the tack. Thus, it can be clear to the physician where all of the markers are and which is which. For example, the pusher bands 44 can be axially longer than the marker 28 on the outer sheath and the marker on the tack. Further, the markers on the delivery device can be bands, while the marker(s) on the tack can be dots.

Looking to FIG. 7B, it can be seen that the marker 28 on the outer sheath 12 and the markers 22 on the first tack 2 are aligned and that the distal end of the sheath is positioned at the distal end of the first tack. The delivery device can now be positioned with respect to the lesion for treatment, such as by centering the radiopaque markers at desired location. The sheath can then be withdrawn to place the tack in the desired location.

In some embodiments, the delivery device can have a marker band on the outer sheath positioned proximally from the distal end-one at least half the length of the tack, the tack having a single column of markers at the middle of the device. A method of deployment can include withdrawing the outer sheath until the marker on the outer sheath and the tack to be delivered are aligned, and then aligning these two markers with the middle of the lesion to be treated (or other treatment area) before release of the tack, the release being affected by further withdrawing the outer sheath. It will be understood that markers on the pusher bands 44 can also be used to help align the delivery device before deployment.

The method can be repeated to deliver multiple tacks (see FIG. 7C with tack shown in the compressed state for reference only). In between tack deployment, the delivery device may be moved to a completely different lesion or treatment area, or simply repositioned to ensure space between adjacent tacks once placed.

As discussed previously, in some embodiments, simultaneous placement of the entire tack can result upon release of the tack from the delivery device. Further, multiple tacks can placed as desired in a distal to proximal placement within the treatment segment of the vessel.

In some embodiments an expandable tack, such as that shown in FIGS. 3 & 3A, can exert a relatively constant force to a wide range of vessel lumen diameters, thereby allowing a single delivery catheter to deploy multiple tacks to varying sized vessels. Ideally the tack can be designed to treat vessels ranging in size from 2 to 8 mm, although other sized tacks could be delivered. It is desirable that the force applied by the tack to the vessel varies 5 N or less over a 3 mm expansion range. More ideally the force applied will vary 1.5 N or less over a 3 mm expansion range.

There are instances where drug coated balloons are being used as an alternative to placing a stent in the vessel. The balloon can dilate narrowing in the vessel and the drug helps to minimize post inflation inflammatory response which can lead to a re-narrowing of the artery. There is clinical evidence that the combination of a balloon and drug can provide an alternative to the implantation of a typical stent which have been historically used to provide both short term and long term scaffolding. Drug coated balloons are desirable in that there is no long term implant placed in the vessel. There are instances however when the expansion of a drug coated balloon may cause damage to the vessel in the form of a tissue dissection in which case a flap or piece of tissue extends into the lumen of the vessel. The dissection can occur within the balloon treatment zone as well as outside of or adjacent to the treatment zone. In these instances it is helpful to tack the dissected tissue against the arterial wall. A tack having a low outward force can beneficially be used to treat the dissection where a stent may not be appropriate, or desirable.

In some embodiments, the precise placement of the tack can be set upon positioning of the catheter within the vessel based on the position of a marker. Once positioned, one or more tacks can then be deployed while maintaining the catheter in place and slowly removing the outer sheath.

In some embodiments, one or more tacks can be deployed at a dissection of tissue. When an angioplasty procedure is performed there are typically one of three outcomes: 1) an optimal outcome, no further stenting or over treatment needs to be performed, 2) residual stenosis, usually requiring the placement of a stent to prop open or scaffold the vessel so that it remains open and does not return to the prior occluded or partially occluded state, and 3) a tissue dissection. A tissue dissection can be where the vessel experiences trauma such as the disruption of an arterial wall resulting in separation of the intimal layer. This may or may not be flow limiting. One or more tacks can beneficially be deployed at such a tissue dissection. Small tacks allow for the treatment of a subset of the portion of the blood vessel treated by the balloon angioplasty procedure thereby providing a treatment therapy with does not require the implantation of long metal stents over the entire angioplasty treatment area. Ideally, one or more tacks could be used to treat 60% or less of the length of vessel in the angioplasty treatment area. Small tacks having a single (illustrated) or double column of cells, have been shown to cause less injury and to have shorter recovery times than commonly available stents in treating tissue dissections.

Upon placement of the tack, an intravascular construct is formed in situ. The in situ placement can be in any suitable vessel, such as in any peripheral artery. The construct need not be limited to just two tacks. In fact, a plurality of at least three intravascular tacks can be provided in an intravascular construct formed in situ. In one embodiment each tack has a length of no more than about 8 mm, e.g., about 6 mm in an uncompressed state. In one configuration, at least one of, e.g., each of, the tacks are spaced apart from an adjacent tack by at least about 4 mm, or between about 4 mm and 8 mm or between about 6 mm and 8 mm. Although certain embodiments have a length of 8 mm or less, other embodiments can be longer, e.g., up to about 12 or 15 mm long. Also, neighboring tacks can be positioned as close as 2 mm apart, particularly in vessels that are less prone to bending or other movements. In some embodiments, a delivery device can be preloaded with six tacks, each about 6.5 mm long, and can be used to treat lesions up to 15 cm in length.

In the various delivery devices described herein, the spacing between implanted tacks can be controlled to maintain a set or a minimum distance between each tack. As can be seen, the delivery devices and/or tacks can include features that help maintain the desired distance between tacks. Maintaining proper inter-tack spacing can help ensure that the tacks are distributed over a desired length without contacting each other or bunching up in a certain region of the treated vessel. This can help to prevent kinking of the vessel in which they are disposed.

While a three tack construct formed in situ may be suitable for certain indications, an intravascular construct having at least 5 intravascular tacks may be advantageous for treating loose plaque, vessel flaps, dissections or other maladies that are significantly more elongated (non-focal). For example, while most dissections are focal (e.g., axially short), a series of dissections may be considered and treated as a more elongated malady.

In some cases, even shorter axial length tacks can be used to treat even more spaced apart locations. For example, a plurality of tacks, each tack having a length of no more than about 7 mm, can be placed in a vessel to treat a tackable malady. At least some of the tacks can be spaced apart from an adjacent tack by at least about 5 mm. In some cases, it may be preferred to provide gaps between adjacent tacks that can range from about 6 mm to about 10 mm.

Optionally, once the tacks are in place, the angioplasty balloon can be returned to the treatment site and inflated to expand the tacks to the desired state of expansion.

Figure 8:
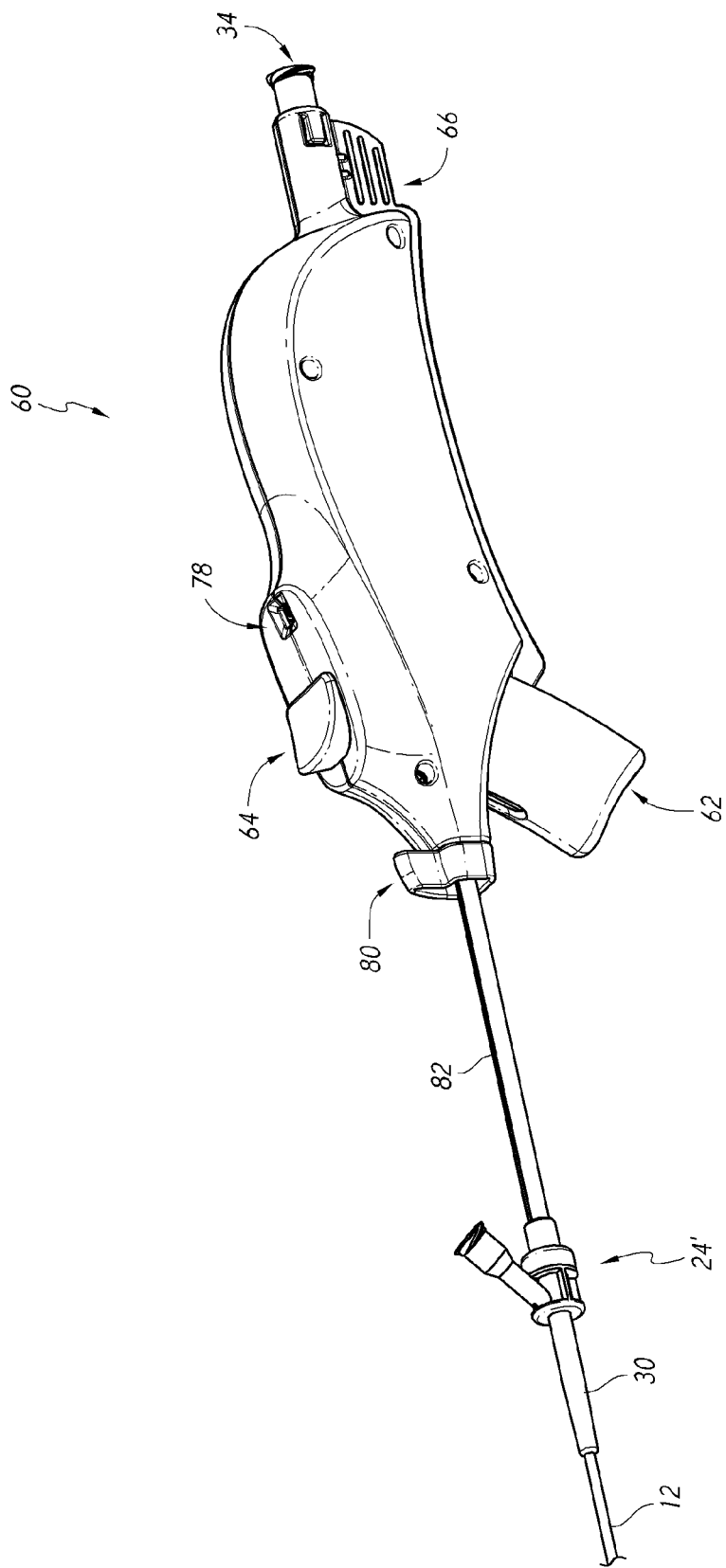
FIG. 8 shows a handle at a proximal end of another embodiment of delivery device.

Turning now to FIG. 8, an embodiment of a handle 60 for a delivery device is shown. The handle 60 can be used for controlled sequential delivery of tacks 2. The handle 60 can beneficially provide the physician with a single-handed method of tack delivery, while also providing increased precision in placement with consistent results, among other benefits.

The handle 60 can include a trigger 62 to control withdrawal of the outer sheath 12. For example, each actuation of the trigger 62 can withdraw the outer sheath to expose a tack 2 and at least a portion of a delivery platform 8. The handle can also include a number of other features, such as safety features 64, 66, a counter 78, a proximal luer hub 34, and a retraction override 80. The functioning of the various features of the handle will be discussed in more detail below. It will be understood that certain embodiments may include one or more of the described features.

The handle 60 can include one or more safety features to prevent premature withdrawal of the outer sheath 12, such as by undesired actuation of the trigger 62. For example, the handle 60 can include a safety button 64 that requires actuation at the same time as or before actuating the trigger 62. Further, the handle can include an interlock 66. The interlock 66 can prevent actuation of the trigger, but can also help maintain the relationship of the outer sheath 12 and inner shaft 26.

Figure 9:
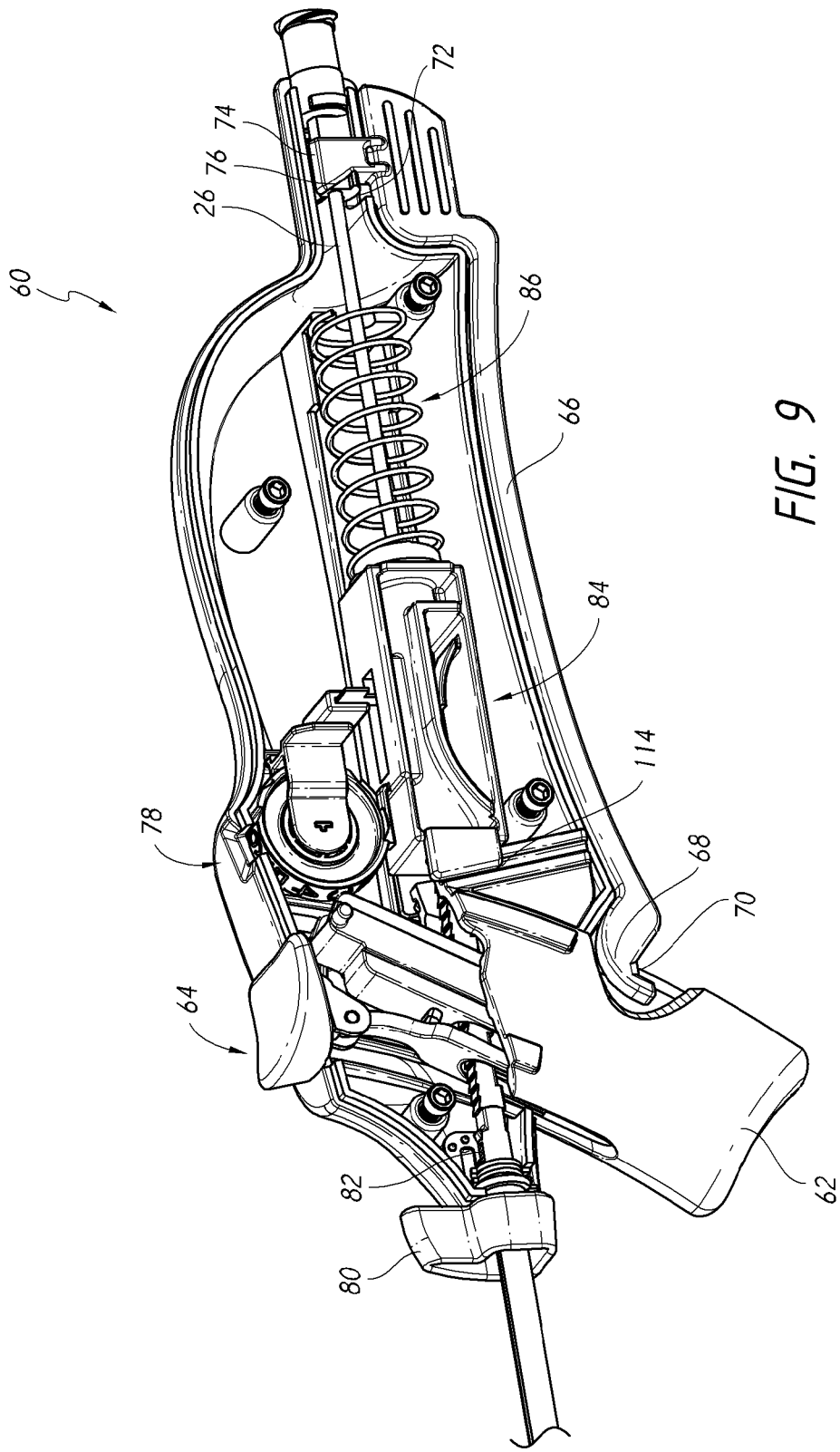
FIG. 9 is a partially disassembled view of the handle of FIG. 8.

Looking now at FIG. 9, the interlock 66 can be seen in more detail. The interlock 66 can remain in place until the physician is ready to deploy the tacks 2. It can hold the inner shaft 26 in place and prevents movement of the trigger 62 which is mechanically linked to the outer sheath 12. In the illustrated embodiment, the interlock 66 releases complete engagement with the handle 60 when removed.

The interlock 66 is shown engaging the trigger 62, the housing of the handle 60 and the inner shaft 26. The interlock 66 can engage a slot 70 on the trigger and a slot 72 on the handle body. In some embodiments, opposite ends 68, 74 of the interlock 66 can be used to separately engage the trigger slot 70 and the handle slot 72. Each end 68, 74 may simply prevent movement of the inner shaft in one direction, or it can prevent movement in two directions.

The interlock can be shaped to allow connection and disconnection in a consistent manner, such as in a first in-last out configuration. As shown, the distal end 68 of the interlock 66 can extend into the trigger and requires rotation downward of the interlock 66 for removal. In some embodiments, distal end 68 of the interlock is hook shaped. The proximal end 74 can include a protrusion that advances into the slot 72. It will be understood that this arrangement can be flipped and that the interlock 66 can connect in other ways.

Further, in some embodiments, releasing the interlock 66 can also advance the inner shaft 26 within the outer sheath 12. This can help reposition and adjust the relationship between the inner shaft 26 with its delivery platforms 8 and the outer sheath 12. It can position the outer sheath in a ready position prepared for tack deployment. The interlock 66 and the inner shaft 26 can have a ramp interface 76. The ramp interface 76 can include a ramp on one or both of the interlock and the inner shaft. For example, in some embodiments, the shuttle interlock can include a ramp on the protrusion 74 and the inner shaft can include a rounded surface that interfaces with the ramp, but does not include an actual ramp.

Removing the interlock 66 with a ramp interface 76 can force the inner shaft 26 to move distally in order for the ramp on the interlock 66 to come out of the slot 72 in the handle housing. It can experience about 6 mm of travel according to some embodiments, this can be a significant movement as the tacks of some embodiments are 6.5 mm long as has been previously discussed.

It will be understood that during advancement of the distal end of the delivery device within the vasculature, the outer sheath and the inner shaft will experience different forces due to friction and the tortuosity of the vessel. This initial adjustment of the inner shaft 26 can help to rebalance the system, as well as moving the first delivery platform to the second pre-deployment position. Also, having the first delivery platform spaced proximally prior to deployment can help to ensure that the first tack is not prematurely released.

The inner shaft 26 can be bonded to the proximal luer hub 34 which can be fixed to the handle housing. This can prevent movement of the inner shaft 26 relative to the outer sheath 12 at the proximal end, though the distal end may experience some relative movement as has been mentioned.

Turning now to FIG. 10, it can be seen that the interlock 66 if part of the embodiment has been removed. The trigger 62 and safety button 64 can now be actuated. The safety button 64 can be connected to a safety release yolk 88. The yolk 88 can pivot at points "P", such that advancing the safety button 64 pivots the yolk away from a protrusion or notch 90 in the trigger 62. Engagement between the yolk 88 and the protrusion 90 prevents the trigger from advancing. Once the yolk is out of the way, the trigger is free to move as can be seen in FIG. 11. It will be understood that the safety features can function in many other ways while providing similar benefits.

Reviewing FIGS. 10 and 11, it can also be seen that the trigger 62 advances along a curved path. The handle housing can comprise an arcuate channel and the trigger can be positioned within the arcuate channel to move in an arcuate path. The trigger 62 can be spring loaded to bias it to the first extended position of FIG. 10, or starting position. Actuation of the trigger can compress the spring 86 and cause the trigger to advance into the handle housing. This action of the trigger can be assisted by a lever 92. The lever 92 can have a pin or other protrusion 94 positioned within a slot 96 in the handle body. As the trigger 62 advances upward, the pin 94 can slide forward in the slot 96. This can help so that the trigger does not bind up as it advances.

In some embodiments, control device can be provided for deploying a self-expanding medical device within the vessel of a living being. The control device can comprise a restraining sheath and a control mechanism or trigger. The restraining sheath can have a proximal end and a distal end, the restraining sheath being adapted to extend over one or more self-expanding medical devices to maintain the medical devices in a collapsed position and to be retractable to expose the one or more collapsed medical devices for deployment. The control mechanism can include an actuation assembly coupled to the proximal end of the restraining sheath for retracting the restraining sheath, a slider assembly being movable in an arcuate path of motion, the retraction of the restraining sheath being actuated by an actuating force applied by a user to a movable component of the control mechanism which moves in an arcuate path thereby changing the angle of force application and the mechanical advantage of the force applied by a user depending on the location of the movable component along the arcuate path.

Advancement of the trigger 62 can also cause movement of a shuttle 84. The shuttle 84 can be mechanically linked connected to the outer sheath 12. Thus, advancement of the shuttle 84 can cause advancement of the outer sheath 12 to thereby withdraw the outer sheath 12 and deploy a tack 2. Each full actuation of the trigger 62, moving from a starting position to an end position, can cause the outer sheath 12 to withdraw sufficiently to deploy a tack and remain in the withdrawn position. The shuttle 84 can also be spring loaded by a return spring 86. This can cause the shuttle 84 to return to its original or starting position after actuation of the trigger, while the outer sheath remains in its withdrawn position.

Thus, each advancement of the trigger 62 further withdraws the outer sheath 12 from the distal end of the inner shaft 26. This can be seen by reviewing FIGS. 10A, 11A and 12A which represent a portion of the distal end of the delivery device when the handle is in the respective first, second, and third positions of FIGS. 10, 11, and 12.

Figures 12, 12A:
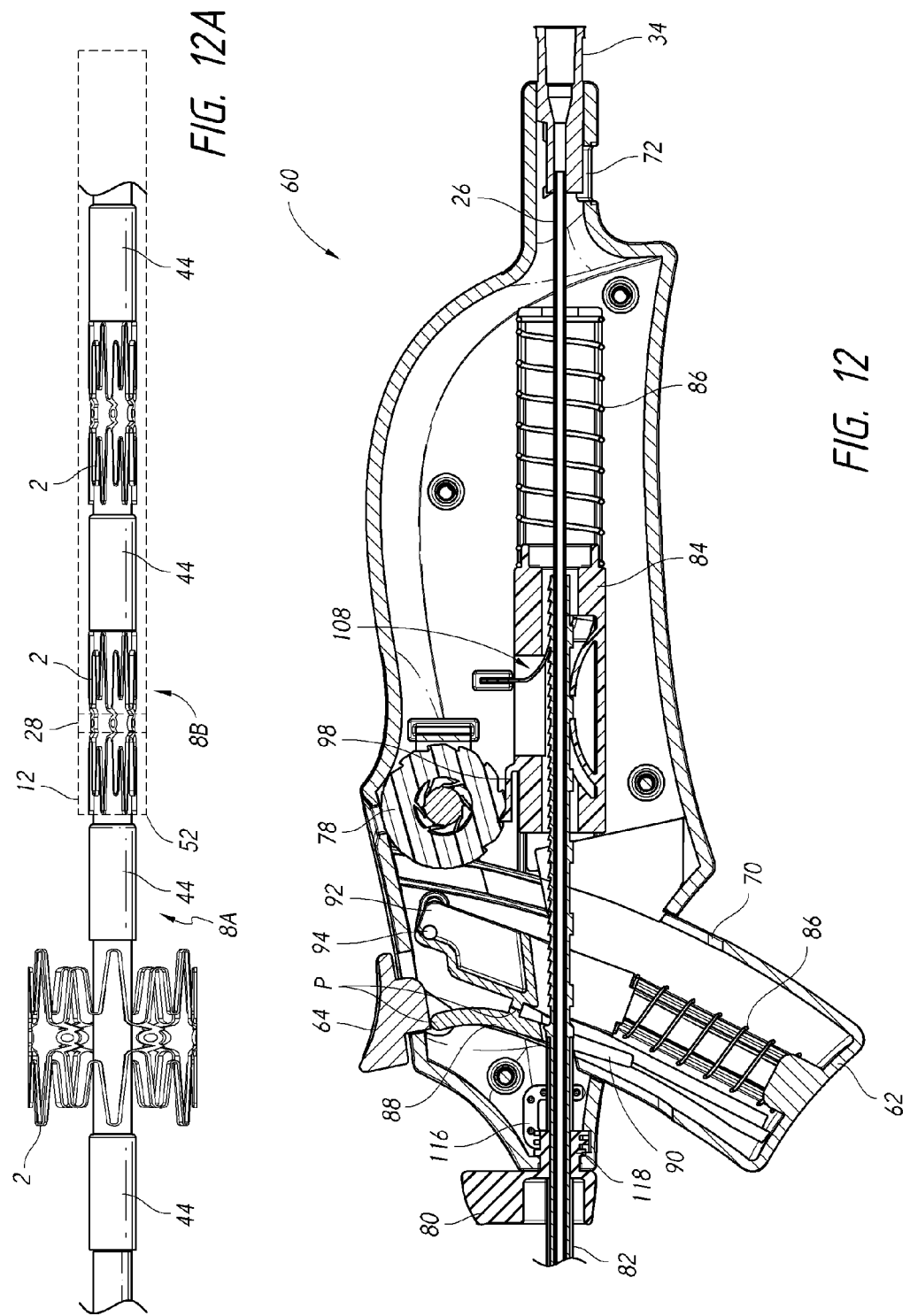
FIG. 12 is a side view of the handle of FIG. 9 in a third position.
FIG. 12A is a representation of a portion of the distal end of the delivery device when the handle is in the third position of FIG. 12.

When the shuttle returns to the initial position, the shuttle can engage a counter 78. The counter 78 can be a type of ratchet, such that each engagement by the shuttle can ratchet the counter in the same direction, counting down the number of tacks that are available to deploy. In some embodiments, the shuttle comprises a counter pawl 98. The counter pawl 98 can engage a different tooth on the counter 78 every time the shuttle returns to the initial position. Reviewing FIGS. 10, 11, and 12 it can be seen that the counter pawl 98 engages a tooth on the counter 78 and then disengages (FIG. 11) as the shuttle is advances, and then engages a new tooth, causing the counter to advance or rotate (FIG. 12).

Figure 10B:
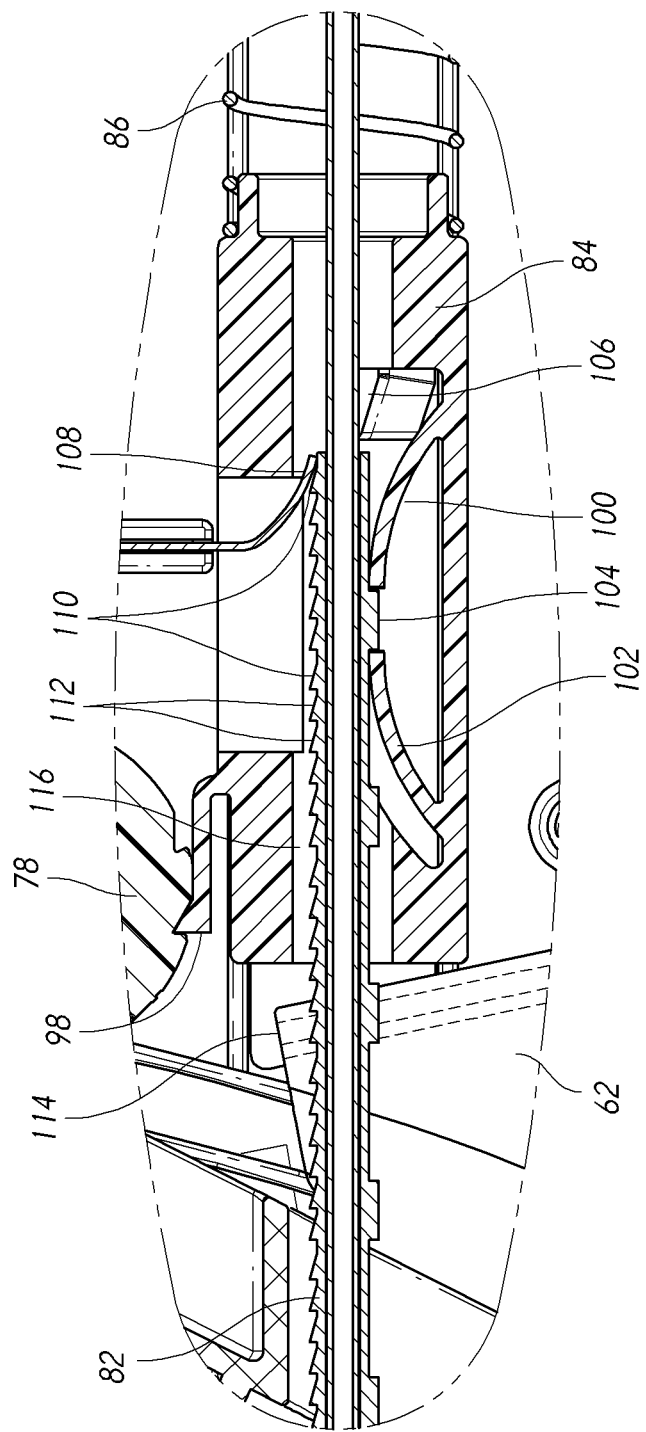
FIG. 10B is a detail view of a portion of the handle showing a shuttle.

Turning now to FIG. 10B, a detail view of the shuttle 84 is shown. The proximal end of the outer sheath can include an outer sheath rack 82. The rack can include a number of teeth 104, 110, 112 as will be described in more detail below. The shuttle can engage and disengage with the teeth 104 to advance the outer sheath rack 82 thereby withdrawing the outer sheath from the distal end of the inner shaft 26. A pawl 108 on the handle housing can engage one or more of teeth 110, 112 to maintain the outer sheath in the withdrawn position.

The rack 82 can include one or more sets of teeth. As shown, the rack includes a top set of teeth 110, 112 and a bottom set of teeth 104. Both sets of teeth work to secure the outer sheath in place, though the top set of teeth are more specifically designed to prevent the rack from reversing direction, and the bottom set of teeth are designed to govern advancement and withdrawal of the rack 82 by the shuttle. The shuttle 84 can include one or more deflection members 100, 102. In the detail view it can be seen that that shuttle 84 includes a pair of deflection members 100, 102.

In an initial position, the deflection members 100, 102 can be positioned on either side of a tooth 104. This can prevent the rack 82 from moving with respect to the housing. The trigger 62 and shuttle 84 can be mechanically linked so that actuation of the trigger 62 causes advancement of the shuttle 84. As best seen in FIGS. 9 & 10B, the trigger and shuttle 84 have a ramped interface 114. Ramps and/or angled surfaces at the ramped interface 114 cause the shuttle to advance proximally as the trigger moves upwards along the curved path. A protrusion 106 on the housing contacts the deflection member 100 as the shuttle advances. This allows the tooth 104 to move past the deflection member 100 as the deflection member 100 is force downwards as can be seen in FIG. 11. The pawl 108 engages the teeth 110, 112 on the top of the rack 82 to prevent the rack from moving distally after actuation of the trigger 62. Once the shuttle returns the initial position, the deflection members 100, 102 engage a new tooth 104, as can be seen in FIG. 12. Looking at FIGS. 10-12A, it can be seen how the trigger and shuttle work through deployment of a first tack.

In some embodiments the rack 82 can include features that can allow for re-sheathing of the tack after a partial actuation of the trigger. For example, the pitch on a first tooth 110 can be increased as compared to other teeth 112. This can allow the user to start actuating the trigger and then re-sheath the tack. In the illustrated embodiment, the user has the ability to release the trigger at approximately ⅙ of the trigger travel (~1 mm of tack exposed) and the outer sheath is able to re-sheath the tack. Once the trigger is actuated beyond ⅙ of travel the pawl 108 engages the next tooth 112 on the rack and prevents the outer sheath from re-sheathing the exposed tack. However, the pawl engagement on the rack does give the user the opportunity to release the trigger during partial deployment while maintaining its position in the event the delivery device needs to be repositioned. In other embodiments, the trigger can be released and the tack re-sheathed after about ½, ⅓, ¼, or ⅕ of the trigger travel. In some embodiments, the rack has a series of teeth with a first tooth 110 having a greater pitch than adjacent teeth 112. In some embodiments, the rack can have a space between a first set of teeth and a second set of teeth. For example, the tooth 110 can be removed from the rack. In some embodiments, one or more teeth on the rack can have a length that is ⅘, ¾, ⅔, ½, 40% ⅓, 30%, ¼ the length of the shortest strut on the distal-most end of the tack. Alternatively, two adjacent teeth can be spaced apart ⅘, ¾, ⅔, ½, 40% ⅓, 30%, ¼ the length of the shortest strut on the distal-most end of the tack. For example, a short strut can be 2 mm long and a tooth can be 1 mm long.

Figure 13:
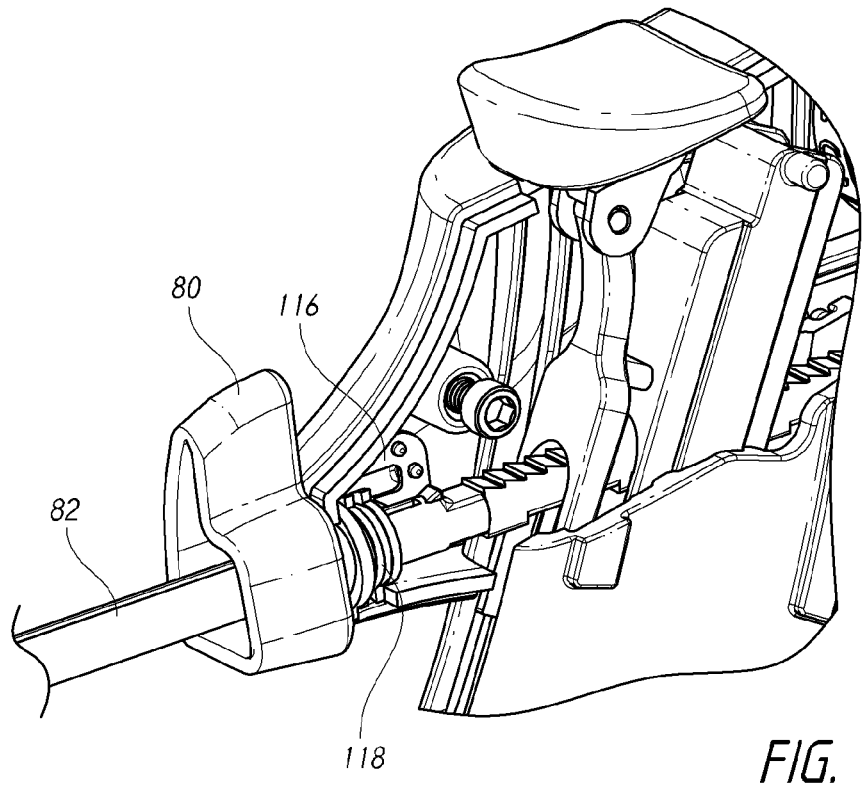
FIG. 13 shows a detail view of a retraction override switch in a first position.
Figure 14:
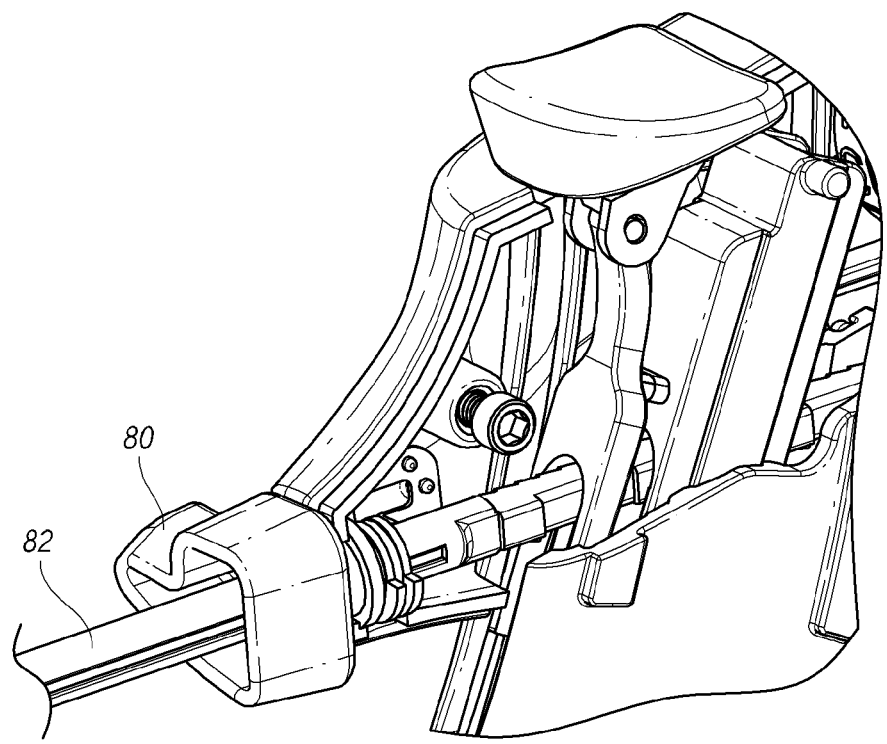
FIG. 14 shows a detail view of a retraction override switch in a second position.
Figure 15:
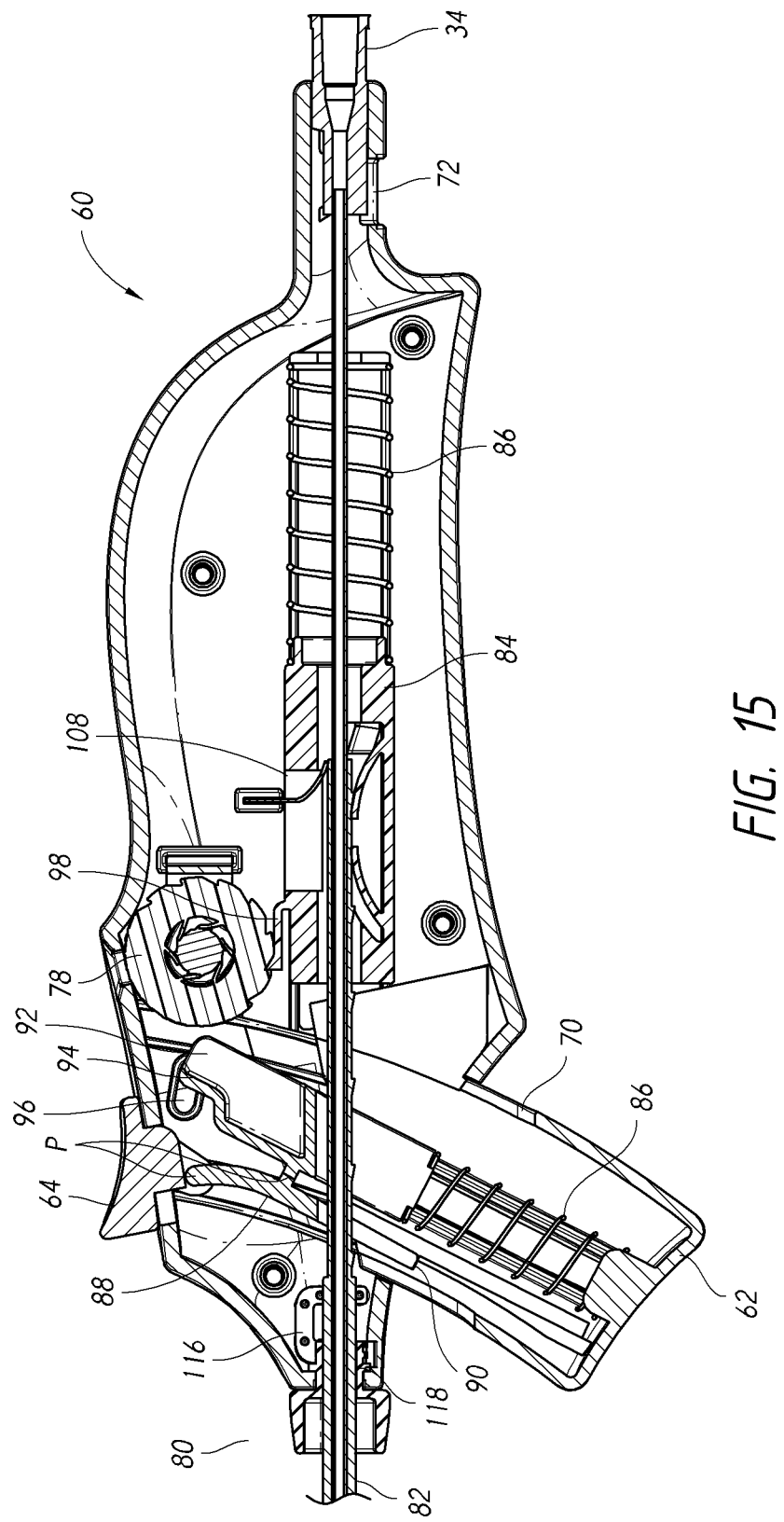
FIG. 15 shows a side view of the handle of FIG. 9 wherein the inner shaft has been re-sheathed by the outer sheath.

Turning now to FIGS. 13-15, re-sheathing after deployment will now be described. After a physician has determined that the delivery device is no longer needed, such as after delivery of one or more tack, it can be desirable to re-sheath the distal end of the inner shaft 26 with the outer sheath 12. As re-sheathing could incorrectly lead a physician to believe that there are additional tacks that can be deployed, it may also be desirable to lock the outer sheath in place after re-sheathing.

Figure 14A:
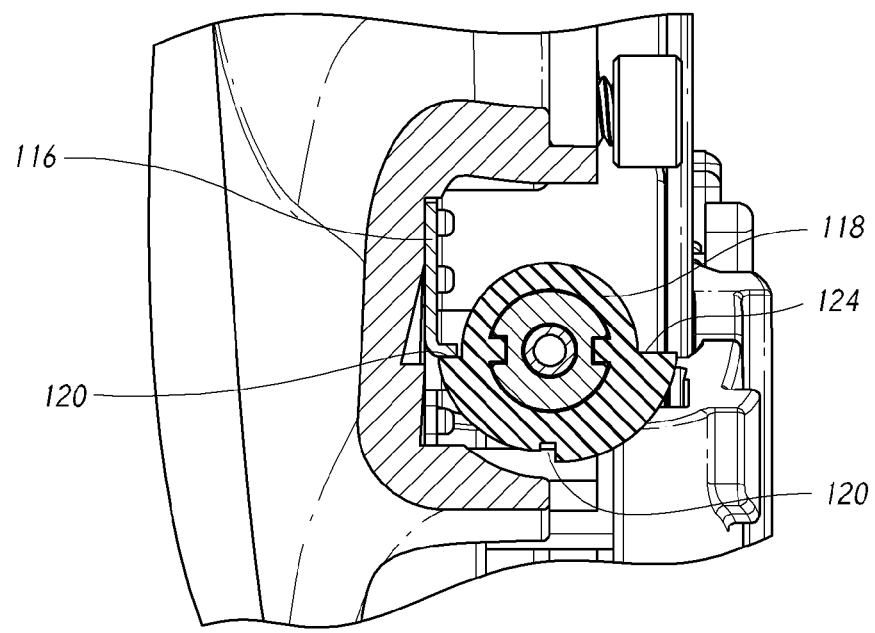
FIG. 14A is a cross-section of the retraction override switch of FIG. 14.
Figure 14B:
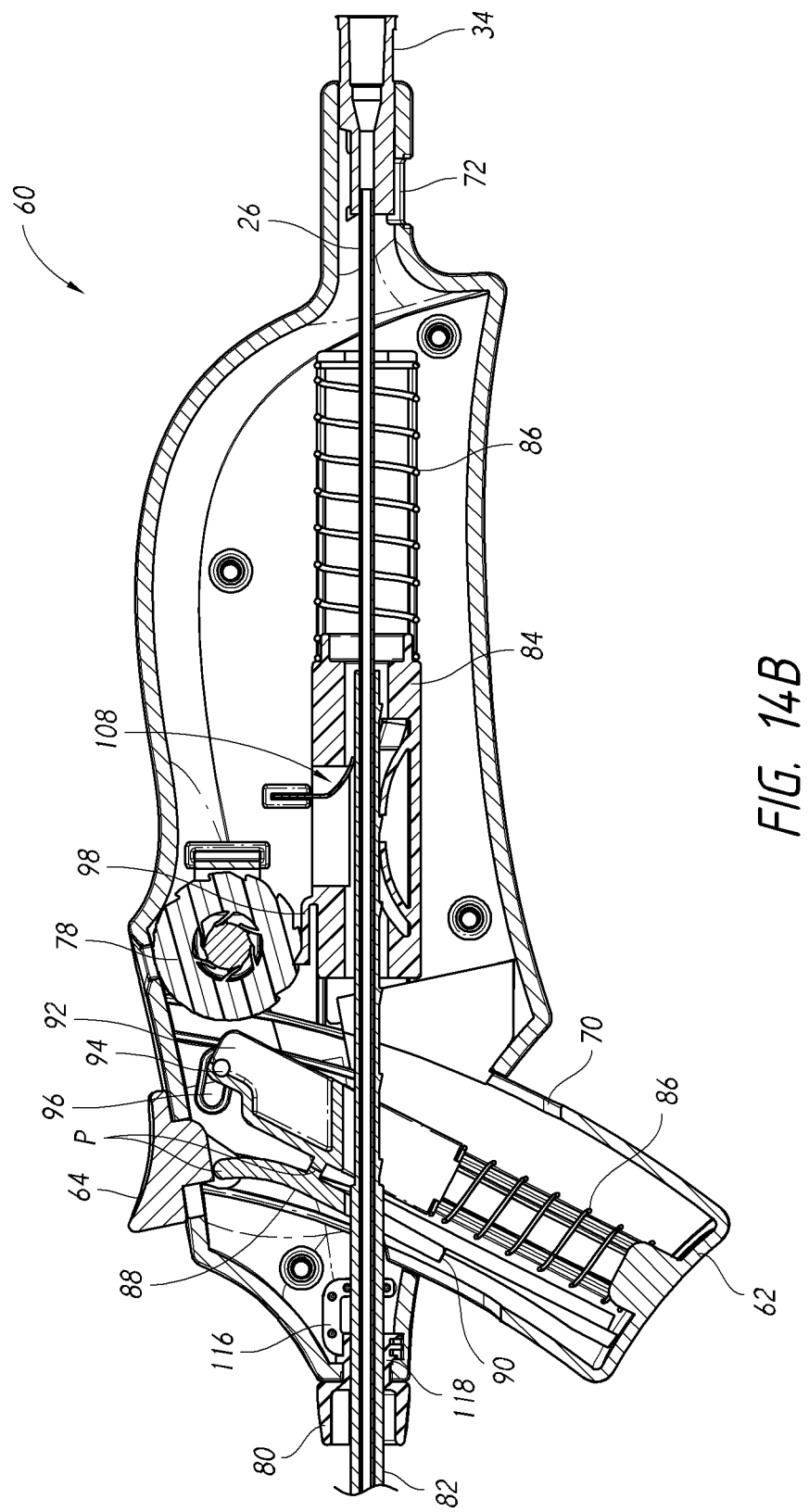
FIG. 14B shows a side view of the handle of FIG. 9 with the retraction override switch in the second position.

The handle 60 can include a retraction override switch 80. Actuation of the retraction override switch 80 can disengage the internal locking features of the handle, such as the pawl 108 and one or more of the deflection members 100, 102. In the illustrated embodiment, the retraction override switch 80 is a rotating lever. Rotation of the lever 80 (FIG. 13 to FIG. 14) turns the teeth 104, 110, 112 on the rack 82 so that they are no longer engaged by the deflection members 100, 102 or the pawl 108 as shown in FIG. 14B. The outer sheath can then be advanced distally to re-sheath the distal end of the inner shaft 26 with the outer sheath 12 as shown in FIG. 15.

Figure 13A:
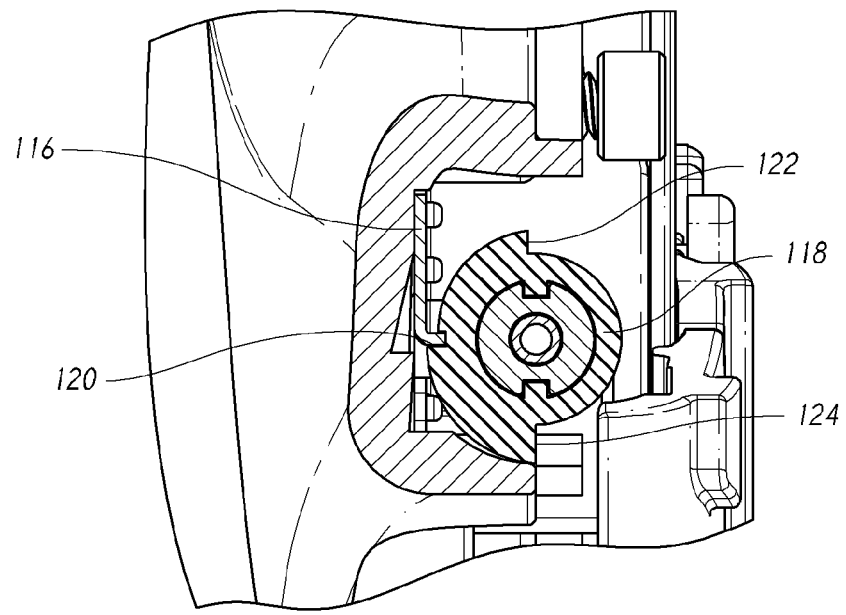
FIG. 13A is a cross-section of the retraction override switch of FIG. 13.

The retraction override switch 80 can also include a locking feature. The locking feature can be used to ensure that the trigger cannot engage the rack after re-sheathing. Looking now to FIGS. 13A and 14A an embodiment of the locking feature is shown. In FIG. 13A, the retraction override switch 80 is in a first disengaged position. A spring loaded member 116, such as a spring steel plate, can engage one or more protrusions and/or slots on the retraction override switch 80. The one or more protrusions and/or slots can be on a cam 118 that rotates as part of the retraction override switch 80. The cam 118 can have a first slot 120 that can engage the spring loaded member 116 during initial use of the handle, such as during actuation of the trigger. Once the desired tacks have been deployed, the retraction override switch 80 can be rotated, causing the cam to rotate. The slot 120 can become disengaged with the spring loaded member 116. The cam can be rotated until a land 124 contacts a surface (not shown) on the housing. The surface can be a protrusion or other surface features that prevents further rotation of the cam. In that position, a second land 122 can engage with the spring loaded member 116 and prevent the cam from being rotated in the reverse direction back to the prior initial position. In this way the rack can secured on its side so that the trigger no longer works to advance the outer sheath proximally.

The outer sheath 12 can then manually be advanced distally to re-sheath the distal end of the inner shaft 26.

Turning now to FIGS. 16 and 16A, another feature of the delivery device is illustrated. Another embodiment of proximal luer hub 24' is shown. The proximal luer hub 24' can be similar to the proximal luer hub 24 previously described. As will be understood, a sealing arrangement 32 is provided that is integrated into the bifurcation luer hub 24' to receive and seal the proximal end of the space between the inner shaft 26 and the outer sheath 12. The proximal luer hub 24' can include a two piece assembly with a seal housing 128 that attaches to the main housing.

There are a large number of patients with critical lower limb ischemia that are unsuited for distal arterial surgical reconstruction and as a result face major distal amputation. Methods such as balloon angioplasty and stenting provide an option to open the blocked or narrowed arteries of these patients. These techniques generally require some level of vessel patency so that a guide wire and catheter can be advanced to the blockage or narrowing for further treatment. In some patients the vessels are nearly or completely occluded and are therefore unsuitable for many transvascular techniques. Distal venous arterialization is a procedure in which the venous bed is used as an alternative conduit for perfusion of peripheral tissues. Via minimally invasive techniques, the blockage area of an artery is bypassed by using an adjacent venous conduit. Typically the most distal satisfactory artery is used for proximal bypass anastomosis. The venous valves, which function to prevent retrograde flow of blood in the venous system, are rendered incompetent or otherwise destroyed with probes, cutting balloons, Fogarty catheters, and valvulotomes to allow proper functioning as an arterial conduit. Alternatively the valves can be rendered incompetent with a stent or tack which can be delivered with the multi-tack/stent delivery system described herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:
1. A delivery device comprising:
    an inner shaft having one or more delivery platforms for deployment of one or more intraluminal devices;
    an outer sheath surrounding the inner shaft and configured to cover the one or more delivery platforms pre-deployment and to be withdrawn from one of the one or more delivery platforms as part of a deployment of one of the one or more intraluminal devices;

a handle housing having a trigger mechanically linked to the outer sheath such that actuation of the trigger withdraws the outer sheath from covering one of the one or more delivery platforms;

an interlock that when in a locked position is engaged with the trigger and the inner shaft to thereby prevent movement of the outer sheath when the interlock is engaged;

a ramp interface between the interlock and the inner shaft, wherein the ramp interface is configured to adjust the position of the inner shaft relative to the outer sheath when the interlock is removed from engagement with the inner shaft; and wherein the ramp interface comprises a first ramp on a protrusion of the interlock and a second ramp on the inner shaft, wherein sliding disengagement of the first and second ramps forces the inner shaft to move.

2. The delivery device of claim 1, wherein the interlock engages the trigger with a distal end of the interlock and engages the inner shaft with a proximal end.

3. The delivery device of claim 2, wherein the proximal end engages the inner shaft and the handle housing.

4. The delivery device of claim 2, wherein the distal end of the interlock is hook shaped.

5. The delivery device of claim 2, wherein the distal end of the interlock prevents movement of the inner shaft in at least one direction when the distal end of the interlock is engaged with the trigger.

6. The delivery device of claim 2, wherein the proximal end of the interlock prevents movement of the inner shaft in at least one direction when the distal end of the interlock is engaged with the inner shaft.

7. The delivery device of claim 1, wherein the interlock when in the locked position prevents actuation of the trigger.

8. The delivery device of claim 1, wherein the ramp interface comprises a single ramp on one of the interlock and the inner shaft.

9. The delivery device of claim 1, wherein the ramp interface is configured such that disengagement of the interlock from the inner shaft causes the inner shaft to advance distally from the handle housing.

10. A delivery device for deploying a medical implant within a vessel, the delivery device comprising:

an inner shaft having one or more delivery platforms for deployment of one or more medical implants;

an outer sheath having a proximal end and a distal end, the outer sheath adapted to extend over the one or more medical implants on the inner shaft in a collapsed position and to be retractable to expose the one or more collapsed medical implants for deployment;

an interlock that when in a locked position is configured to prevent retraction of the outer sheath; and a handle having:
a control mechanism including an actuation assembly coupled to the proximal end of the outer sheath for retracting the outer sheath with respect to the inner shaft;

one or more slots therein configured to receive the interlock, wherein the delivery device is further configured such that retraction of the outer sheath is prevented when the one or more slots receive the interlock; and an interface configured such that disengagement of the interlock from the interface on the handle causes the inner shaft to advance within the outer sheath.

11. The delivery device of claim 10, wherein the one or more slots include a first slot positioned on the control mechanism and a second slot positioned distally on handle therefrom.

12. The delivery device of claim 11, wherein movement of the inner shaft is prevented in one or more directions when one or more of the first slot and the second slot receive the interlock.

13. The delivery device of claim 11, wherein one or more of the inner shaft and a proximal portion of the interlock comprise a ramp forming the interface, the interface being between the inner shaft and the interlock when the interlock is received in the second slot.

14. The delivery device of claim 11, wherein movement of the control mechanism is prevented in at least one direction when the interlock is received in the first slot.

15. The delivery device of claim 11, wherein the interlock comprises a hook-shaped distal end positioned in the first slot.

\* \* \* \* \*